US008222211B2

(12) United States Patent
Barnea

(10) Patent No.: US 8,222,211 B2
(45) Date of Patent: *Jul. 17, 2012

(54) METHODS OF ADMINISTERING PIF AGONIST PEPTIDES AND USES THEREOF

(75) Inventor: Eytan R. Barnea, Cherry Hill, NJ (US)

(73) Assignee: BioIncept, LLC, Cherry Hill, NJ (US)

(*) Notice: Subject to any disclaimer, the term of this patent is extended or adjusted under 35 U.S.C. 154(b) by 1563 days.

This patent is subject to a terminal disclaimer.

(21) Appl. No.: 10/971,760

(22) Filed: Oct. 22, 2004

(65) Prior Publication Data

US 2009/0081225 A1 Mar. 26, 2009
US 2012/0107318 A9 May 3, 2012

Related U.S. Application Data

(63) Continuation-in-part of application No. 10/482,244, filed as application No. PCT/US02/20599 on Jun. 28, 2002, now Pat. No. 7,273,708.

(60) Provisional application No. 60/513,370, filed on Oct. 22, 2003, provisional application No. 60/302,607, filed on Jul. 2, 2001.

(51) Int. Cl.
A61K 38/00 (2006.01)

(52) U.S. Cl. ...... 514/9.8; 514/12.2; 514/21.4; 514/21.5; 514/21.6; 530/325; 530/868; 424/278.1

(58) Field of Classification Search .................. None
See application file for complete search history.

(56) References Cited

U.S. PATENT DOCUMENTS

| 5,279,941 | A | 1/1994 | Lessey |
| 5,646,003 | A | 7/1997 | Barnea et al. |
| 5,981,198 | A | 11/1999 | Barnea et al. |
| 6,171,591 | B1 | 1/2001 | Hall |
| 6,585,979 | B1 | 7/2003 | Berman |
| 7,273,708 | B2 | 9/2007 | Barnea et al. |
| 7,670,850 | B2 | 3/2010 | Barnea et al. |
| 7,670,851 | B2 | 3/2010 | Barnea et al. |
| 7,670,852 | B2 | 3/2010 | Barnea et al. |
| 7,678,582 | B2 | 3/2010 | Barnea et al. |
| 7,695,977 | B2 | 4/2010 | Barnea et al. |
| 7,723,289 | B2 | 5/2010 | Barnea |
| 7,723,290 | B2 | 5/2010 | Barnea |
| 2003/0099643 | A1 | 5/2003 | June et al. |
| 2005/0064520 | A1 | 3/2005 | Barnea et al. |
| 2008/0003178 | A1 | 1/2008 | Barnea |
| 2008/0269137 | A1 | 10/2008 | Barnea |
| 2008/0293149 | A1 | 11/2008 | Barnea et al. |
| 2008/0299677 | A1 | 12/2008 | Barnea et al. |
| 2008/0305468 | A1 | 12/2008 | Barnea et al. |
| 2008/0305552 | A1 | 12/2008 | Barnea et al. |
| 2009/0011427 | A1 | 1/2009 | Barnea et al. |
| 2010/0197040 | A1 | 8/2010 | Barnea et al. |

FOREIGN PATENT DOCUMENTS

| WO | WO94/06464 A1 | 3/1994 |
| WO | WO 95/26982 A1 | 10/1995 |
| WO | WO95/26982 A2 | 10/1995 |
| WO | WO97/09418 A1 | 3/1997 |
| WO | WO02/053092 A2 | 7/2002 |
| WO | WO 02/053092 A2 | 7/2002 |
| WO | WO 03/004601 A | 1/2003 |
| WO | WO 03004601 A2 * | 1/2003 |
| WO | WO 2004/053086 A | 6/2004 |
| WO | WO 2005/040196 A2 | 5/2005 |

OTHER PUBLICATIONS

Gonzalez et al. "Preimplantation Factors (PIF) Embryo-Derived Immunomodulatory Peptides: Possible Implications for Maternal Recognition and Allograft Tolerance" 2002, American Journal of Reproductive Immunology, vol. 47, No. 6, p. 347.
Schumacher et al. Primer on the Rheumatic Diseases, 10th edition, 1993, Arthritis Foundation, pp. 86-89 and 100-105.
Barnea et al. "Applying Embryo-Derived Immune Tolerance to the Treatment of Immune Disorders" 2007, Annals of the New York Academy of Sciences, 1110: 602-618.
Gonzalez, R.R., et al., Preimplantation Factor (PIF) May Modulate Maternal Cellular Immunity (CD2), SIEP, The Society for the Investigation of Early Pregnancy, BioIncept, Inc., BBRI, Boston Biomedical Research Institute, p. 68-69.
Barnea, Insight into Early Pregnancy Events: The Emerging Role of the Embryo, 2004, Am. J. Reprod. Immunol. 51:319-322.
Stewart et al., Preimplantation Development of Mammalian Embryo and Its Regulation by Growth Factors, 1997, Dev. Genetics 21:91-101.
Rose et al. Manual of Clinical Laboratory Immunology, 5th edition, 1997, ASM Press, pp. 20-48.
Janeway et al. Immunobiology, 3rd edition, 1997, Garland Publishing Inc., pp. 7:25 and 9:31.
Goodnow, "Pathways for Self-Tolerance and the Treatment of Autoimmune Diseases" The Lancet, 2001, 357(9274):2115-2121.
Skyler et al. "Use of Inhaled Insulin in a Basal/Bolus Insulin Regimen in Type 1 Diabetic Subjects" Diabetes Care, 2005, 28(7):1630-1635.
Pozzilli et al. "No Effect of Oral Insulin on Residual Beta-Cell Function in Recent-Onset Type I Diabetes (the IMDIAB VII)" Diabetologia 2000, 43:1000-1004.
Dong et al. "Transplantation Tolerance: The Concept and its Applicability" Pediatric Transplantation, 1999, 3:181-189.

(Continued)

Primary Examiner — Michael Szperka
(74) Attorney, Agent, or Firm — Pepper Hamilton LLP

(57) ABSTRACT

A novel class of embryo derived peptides are described (Preimplantation factor) that were generated synthetically and were tested on peripheral blood immune cells and shown to block activated but not basal immunity, inhibiting cell proliferation and creating a $T_H2$ type cytokine bias. In addition PIF peptides enhance endometrial receptivity by increasing adhesion molecules expression. PIF biological activity appears to be exerted by specific binding to inducible receptors present on the several white cell lineages. PIF peptides, which are immune modulators, therefore may have diagnostic and non toxic therapeutic applications in improving fertility, reducing pregnancy loss as well may be useful when administered for the treatment of autoimmune diseases and for prevention xenotransplants rejection.

15 Claims, 14 Drawing Sheets

OTHER PUBLICATIONS

Bell et al. "In *Trans* T Cell Tolerance Diminishes Autoantibody Responses and Exacerbates Experimental Allergic Encephalomyelitis" The Journal of Immunology, 2008, 180:1508-1516.

Kraus et al. "Oral Tolerance and Inflammatory Bowel Disease" Current Opinion in Gastroenterology, 2005, 21:692-696.

Schroeder et al. "Tolerance and the 'Holy Grail' of Transplantation" Journal of Surgical Research, 2003, 111:109-119.

Chaouat, J. "Control of Fetal Survival in CBA × DBA/2 Mice by Lymphokine Therapy" Journal of Reproducation and Fertility, 1990, 89:447-458.

Tangri et al. "Maternal Anti-Placental Reactivity in Natural, Immunologically-Mediated Fetal Resorptions" Journal of Immunology, 1994, 152:4903-4911.

Marketletter, "AutoImmune Shares Collapse on Colloral Data in Rheumatoid Arthritis" 1999, Marketletter Publications Ltd., 2 pages.

Bodian, DL et al., *Crystal Structure of the Extracellular Region of the Human Cell Adhesion Molecule CD2 at 2.5 A Resolution*, Laboratory of Molecular Biophysics, Oxford, UK, Structure, Aug. 15, 1994, vol. 2(8):755-66 (abstract).

Critser, E.S. et al., *The Role of Platelet-Activating Factor in Reproduction*, Chapter 15 in Immunological Obstetrics, W.W. Norton, New York, 1992, pp. 202-215.

Barnea, *Embryo-Maternal Dialogue: Linking Pregnancy Recognition and Proliferation Control*, Rochester Trophoblast Conference 2000, under the auspices of the Trophoblast Conference and SIEP, the Society for the Investigation of Early Pregnancy, Rochester, NY.

Ripka et al., Peptidomimetic design, 1998, Curr. Op. Chem. Biol. 2:441-452.

Hrbuy et al., Synthesis of oligopeptide and peptidomimetic libraries, 1997, Curr. Op. Chem. Biol. 1:114-119.

Hruby et al., Conformational and topographical considerations in designing agonist peptidomimetics from peptide leads, 2000, Curr. Med. Chem. September. 7(9): 945-970.

Barnea et al., *Progress in characterization of pre-implantation factor in embryo cultures and in vivo*, 1999, Am. J. Reprod. Immunol. 00.

Barnea, *The Embryo: a privileged entity in a privileged site: lessons learnt from embryonal development*, 1997, Early Pregnancy: Biol. & Med., 3:77-80.

Barnea, *Current Progress in Early Pregnancy Investigation and the Steps Ahead Part I*, 2000, Early Pregnancy Biology & Medicine, 4:1-4 (SIEP Publ @ www.earlypregnancy.org).

Barnea et al., *Embryo-maternal signaling prior to implantation*, 2001, in Obstetrics & Gynecology, Section 2 Human Reproduction—Anatomy, Physiology, Embryology, Munteanu Ed. (Romanian Academy of Science Publishers), pp. 112-117.

Roussev et al., *Embryonic origin of preimplantation factor (PIF): biological activity and partial characterization*, 1996, Mol. Human Reprod., 2, No. 11:883-887.

Barnea, *EnVision the field of Early Pregnancy Investigation*, 1995, Early Pregnancy: Biol. & Med., 1:169-170.

Rayburn, *Embryonic Medicine and Therapy*, 1999, (Jauniaux, E., Barnea, E.R., Edwards, R.G., eds.) The New England Journal of Medicine Book Review, 340(19):1519.

Barnea, Keynote Editorial: *New Frontiers in Early Pregnancy Investigation*, 1995, Early Pregnancy: Biol. & Med. 1:1-3.

Barnea et al., Editorial: *Reflections on early pregnancy: organizing chaos or organized chaos?*, 1996, Early Pregnancy: Biol. & Med. 2:77-79.

Barnea et al., *Use of Lymphocyte Platelet Binding Assay for Detecting a Preimplantation Factor: A Quantitative Assay*, 1994, Am. J. Reprod. Immunol. 32:133-138.

Boklage, *Survival probability of human conceptions from fertilization to term*, Int J Fertil, Mar.-Apr. 1990 35(2): 75, 79-80, 81-94.

Barnea et al., *Immune System (IS) and Proliferation Control (PC) from Embryo to Adulthood: Roles of Preimplantation Factor (PIF) * and Developmental Proteins (DPs)*, 2001, Renaissance Congress of the 21st Century: The Woman and Child Before, During and After Pregnancy, A Global union of Scientific Congresses, under the high patronage of the President of the Italian Republic, 5th SIEP World Conference, 1st International Congress of the Mediterranean Society of Reproduction and Neonatology, 4th International Congress of the International Society for New Technology in Gynecology, Reproduction and Neonatology, Rome, Italy.

Coulam et al., 1995, *Preimplantation factor (PIF) predicts subsequent pregnancy loss*, Am. J. Reprod. Immunol. 34:88-92.

Gonzalez et al., *Preimplantation Factor (PIF) May Modulate Maternal Cellular Immunity (CD2)*, SIEP, The Society for the Investigation of Early Pregnancy, American Journal of Reproductive Immunology, (Jul. 2001) vol. 46, No. 1, pp. 68-69.

Barnea et al., *Embryonic Signals*, in Jauniaux, 1997, Jauniaux, E., Barnea, E.R., Edwards, R.G. (eds.) Embryonic Medicine and Therapy, pp. 63-75 (Oxford University Press).

Barnea, *Underlying mechanisms and treatment of early pregnancy failure*, 2001, Ferti Magazine, Ferti.Net Worldwide Fertility Network, Apr. 1-4.

Navot et al., *Poor oocyte quality rather than implantation failure as a cause of age-related decline in female fertility*, Lancet, Jun. 8, 1991: 337(8754):1375-1377 (abstract).

Mirhashemi, *Cancer and Pregnancy*, 2002, (Barnea, E.R., Jauniaux, E., Schwartz, P.E., eds.) New England J Med Book Review, Jun. 13, 346(24):1921.

Roussev et al., A Novel Bioassay for Detection of Preimplantation Factor (PIF), 1995, Am J Reprod. Immunol. 33:68-73.

Roussev et al., *Development and Validation of an Assay for Measuring Preimplantation Factor (PIF) of Embryonal Origin*, 1996, Am. J. Reprod. Immunol. 35:281-287.

Barnea et al., 2000, *Maternal Immune Response to Trophoblast*, GTD and Cancer, In: Shoenfeld, Y. and Gerhwin, M.E. (eds) Cancer and Autoimmunity, pp. 343-350, Elsevier Science B.V. Publishers.

Barnea et al., *Identification and Validation of an Assay for Preimplantation Factor (PIF)*, 1994, Society for Gynecologic Investigation 41st Meeting, April, Chicago, IL (abstract).

Roussev et al., *Clinical Validation of Preimplantation Factor (PIF) Assay*, 1994, Second World Conference on Implantation and Early Pregnancy in Humans, May, Atlantic City, NJ (abstract).

Roussev et al., 1994, *A Novel Bioassay for Detection of Preimplantation Factor (PIF)*, American Society of Reproductive Immunology, XVI Annual Meeting, June, Philadelphia, PA (abstract).

Coulam et al., *Preimplantation Factor (PIF) Predicts Subsequent Pregnancy Loss*, 1994, The American Fertility Society 50th Annual Meeting, November, San Antonio, TX (abstract).

Roussev et al., *Embryonic Origin of Preimplantation Factor (PIF)*, 1995, Society for Gynecological Investigation 42nd Meeting, Chicago, IL (abstract).

Barnea et al., *Partial Characterization of Embryo-Derived Preimplantation Factor (PIF)*, 2006, Ninth World Congress on Human Reproduction, May, Philadelphia, PA (abstract).

Barnea et al., *Preimplantation Factor (PIF): Current Developments*, 1996, Third World Conference on Early Pregnancy—An Interdisciplinary Approach, October, Atlantic City, NJ (abstract).

Barnea et al., 1998, *Partial Characterization of Mammalian Preimplantation Factor in Culture and In Vivo*, Fourth International Meeting Mechanisms in Local Immunity: and Joint Meeting Fourth Meeting of Alps Adria Society for Immunology of Reproduction (AASIR), September, Opatija, Croatia (abstract).

Barnea, *Preimplantation Factor: A specific embryo viability factor*, 1999, The First National Congress on Human Assisted Reproduction with International Participation under the patronage of the Romanian Academy, Timisoara, Romania (abstract).

Gonzales et al., *Preimplantation factor (PIF) could be a portion of CD2 or a homologue peptide*, 2001, 57th Annual Meeting of the American Society for Reproductive Medicine, Orlando, FL (abstract).

Barnea, *Safeguards established at conception influence peri and postnatal life: Roles of Preimplantation Factor (PIF) and Developmental Proteins (DPs)*, 2001, World Congress of Perinatal Medicine, Parallel Scientific SIEP Meeting, Sep. 23-27, Barcelona, Spain (abstract).

Barnea, *Novel Preimplantation Factors (PIF) and Developmental Peptides (DPs) are involved in safeguarding pregnancy*, 2002, The Fetus as a Patient, Budapest, Hungary (abstract).

Gonzales et al., *Preimplantation factors (PIF) embryo-derived immunomodulatory peptides: possible implications for maternal rec-* ognition and allograft tolerance, 2002, 22nd Annual Meeting of the American Society for Reproduction Immunology, Chicago, IL (abstract).

Gonzalez et al., Immunomodulatory features of preimplantation factors (PIF) from mouse embryos, 2002, 11th World Conference on Human Reproduction, June, Montreal, Canada.

Paidas et al, *Pregnancy Implantation Factor (PIF) Activity is Correlated with a Pro-Inflammatory Response*, 2002, 23rd Annual Society for Maternal-Fetal Medicine Conference, San Francisco, CA (abstract).

Barnea et al., Identification and Validation of an Assay for Preimplantation Factor (PIF), 1994, Second World Conference on Implantation and Early Pregnancy in Humans, May, Atlantic City, NJ (abstract).

Gardner et al., Culture of viable human blastocysts in defined sequential serum-free media, 1998, Human Reprod. June: 13, Suppl 3: 148-159.

Barnea et al., *Preimplantation Signalling by the Embryo*, 3rd World Conference on Early Pregnancy, Oct. 3-6, 1996 (abstract).

Raghupathy, The 1-type immunity is incompatible with successful pregnancy, 1997, Immunol. Today 18: 478 (abstract).

Wegmann et al., Bidirectional cytokine interactions in the maternal-fetal relationship: is successful pregnancy a TH2 phenomenon? 1993, Immunol. Today 14, 353-356 (abstract).

Cavanagh et al, The purification of early-pregnancy factor to homogeneity from human platelets and identification as chaperonin 10, 1994, Eur. J. Biochem. 222: 551-560 (abstract).

Piccinni et al., Production of IL-4 and leukemia inhibitory factor by T cells of the cumulus oophorus: a favorable microenvironment for pre-implantation embryo development, 2001, Eur. J. Immunol., Aug: 31(8), 2431-2437(abstract).

Wickramasinghe et al., Blood and bone marrow changes in malaria, 2000, Baillieres Best. Pract. Res. Clin. Haematol. June:13(2), 277-299 (abstract).

Romagnani, Lymphokine production by human T cells in disease states, 1994, Annu. Rev. Immunol. 12, 227-257 (abstract).

Chaouat et al., IL-10 prevents naturally occurring fetal loss in the CBA × DBA/2 mating combination, and local defect in IL-10 production in this abortion-prone combination is corrected by in vivo injection of IFN-tau, 1995, J. of Immunol. 154, 4261-4268 (abstract).

Ho et al., Distribution of Th1 and Th2 cell populations in human peripher and decidual T cells from normal and anembryonic pregnancies, 2001, Fertil. Steril. Oct:76(4): 797-803 (abstract).

Wu et al., Increase in the production of interleukin-10 early after implantation is related to the success of pregnancy, 2001, Am. J. Reprod. Immunol. Dec:46(6): 386-392 (abstract).

Choudhury et al., Human reproductive failure I: Immunological factors, 2000, Hum. Reprod. Update 7:113-134.

Roussev et al., A Novel Bioassay for Detection of Preimplantation Factor (PIF), 1995, Am. J. Reprod. Immunol. 33: 68-73.

Heyner, Growth factors in preimplantation development: role of insulin and insulin-like growth factors, 1997, Early Preg. Biol and Med 3: 153-163.

Abbas et al., Functional diversity of helper T lymphocytes, 1996, Nature 383: 787-793.

Taubes, Malaria Parasite Outwits the Immune System, 2000, Science 290: 435.

Barnea et al., Implantation in Obstetrics and Gynecology, 2001, Section 2 Human Reproduction-Anatomy, Physiology, Embryology, Munteanu Ed. (Romanian Academy of Science Publishers) pp. 117-123 (TOC only).

Barnea et al., Evolution of the feto-placental unit, 2001in Obstetrics & Gynecology, Section 2 Human Reproduction-Anatomy, Physiology, Embryology, Munteanu Ed. (Romanian Academy of Science Publishers) pp. 170-175.

Barnea, E.R., 2000, *Embryo-Maternal dialogue: linking pregnancy recognition to proliferation control*, Rochester Trophoblast Conference 2000, under the auspices of the Trophoblast Conference and SIEP, The Society for the Investigation of Early Pregnancy, Rochester, NY.

Ripka & Rich, Curr. Op. Chem. Biol. 2:441-452, 1998.

Hrbuy et al., Curr. Op. Chem. Biol. 1:114-119, 1997.

Hruby & Balse, Curr. Med. Chem. 9: 945-970, 2000.

Barnea, E.R., Simon, J.H., Levine, S.P., Coulam, C.B., Taliadouros, G.S., Leavis, P.C., 1999, *Progress in characterization of preimplantation factor (PIF) in embryo cultures and in vivo*, Am. J. Reprod. Immunol. 42(2):95-99.

Barnea, E.R., 1997, Editorial: *The Embryo: a privileged entity in a privileged site: Lessons learnt from embryonal development*, Early Pregnancy: Biol. & Med., 3:77-80.

Barnea, E.R., 2000, Editorial: *Current progress in Early Pregnancy investigation and the steps ahead Part I*, Early Pregnancy Biology & Medicine, 4:104, 4:1-4 (SIEP Publ @ www.earlypregnancy.org).

Barnea, E.R., Choi, Y.J., Leavis, P.C., 2001, *Embryo-maternal signaling prior to implantation*, in Obstetrics & Gynecology, Section 2 Human Reproduction—Anatomy, Physiology, Embryology, Munteanu Ed. (Romanian Academy of Science Publishers), pp. 112-117.

Roussev, R.G., Colam, C.B., Kaider, B.D., Yarkoni, M., Leavis, P.C., Barnea, E.R., 1996, *Embryonic origin of preimplantation factor (PIF): biological activity and partial characterization*, Mol. Human Reprod., 2:883-887.

Barnea, E.R., 1995, Editorial: *EnVision the field of Early Pregnancy Investigation*, Early Pregnancy: Biol. & Med., 1:169-170.

Rayburn, W.F., 1999, *Embryonic Medicine and Therapy*, (Jauniaux, E., Barnea, E.R., Edwards, R.G., eds.) The New England Journal of Medicine Book Review, 340(19):1519.

Barnea, E.R., 1995, Keynote Editorial: *New Frontiers in Early Pregnancy Investigation*, Early Pregnancy: Biol. & Med., 1:1-3.

Barnea, E.R., Schofield, P.N., 1996, Editorial: *Reflections on early pregnancy: organizing chaos or organized chaos?*, Early Pregnancy: Biol. & Med., 2:77-79.

Barnea, E.R., Lahijani, K.I., Roussev, R., Barnea, J.D., Coulam, C.B., 1994, *Use of lymphocyte platelet binding assay for detecting a preimplantation factor: a quantitative assay*, Am. J. Reprod. Immunol. 32:133-138.

Boklage, CE, *Survival probability of human conceptions from fertilization to term*, Int J Fertil 1990, 35:75.

Barnea, E.R., 2001, *Immune system and proliferation control evolution from embryo to adulthood: Roles of preimplantation factor (PIF) * and development proteins (DPs)*, Renaissance Congress of the 21st Century: The Mother and Child, before, during and after pregnancy, A Global union of Scientific Congresses, under the high patronage of the President of the Italian Republic, 5th SIEP World Conference, 1st International Congress of the Mediterranean Society of Reproduction and Neonatology, 4th International Congress of the International Society for New Technology in Gynecology, Reproduction and Neonatology, Rome, Italy.

Coulam, C.B., Roussev, R.G., Thomasson, E.J., Barnea, E.R., 1995, *Preimplantation factor (PIF) predicts subsequent pregnancy loss*, Am. J. Reprod. Immunol. 34:88-92.

Gonzalez, R.R., et al., *Preimplantation Factor (PIF) May Modulate Maternal Cellular Immunity (CD2)*, SIEP, The Society for the Investigation of Early Pregnancy, American Journal of Reproductive Immunology, (Jul. 2001) vol. 46, No. 1, pp. 68-69.

Barnea, E.R., Coulam, C.B., 1997, *Embryonic Signals*, in Jauniaux, E., Barnea, E.R., Edwards, R.G. (eds.) Embryonic Medicine and Therapy, pp. 63-75 (Oxford University Press).

Barnea, E.R., 2001, *Underlying mechanisms and treatment of early pregnancy failure*, Ferti Magazine, Ferti.Net Worldwide Fertility Network.

Navot, D., Bergh, PA, Williams, MA et al. *Poor oocyte quality rather than implantation failure as a cause of age-related decline female fertility*, Lancet 1991, 337:1375 (abstract).

Mirhashemi, R., 2002, *Cancer and Pregnancy*, (Barnea, E.R., Jauniaux, E., Schwartz, P.E., eds.) The New England Journal of Medicine Book Review, 346(46):1921.

Roussev, R.G., Coulam, C.B., Barnea, E.R., 1996, *Development and validation of an assay for measuring preimplantation factor (PIF) of embryonal origin*, Am. J. Reprod. Immunol. 35:281-287.

Barnea, E.R., Levine, S.P., 2000, *Maternal Immune Response to Trophoblast, GTD and Cancer*, In: Shoenfeld, Y. and Gerhwin, M.E. (eds) Cancer and Autoimmunity, pp. 343-350, Elsevier Science B.V. Publishers.

Barnea, E.R., Lahijani, K.I., Roussev, R.G., Barnea, J.D., Coulam, C.B., 1994, *Identification and validation of an assay for preimplantation (PIF)*, Society for Gynecological Investigation 41st Meeting, April, Chicago, IL (abstract).

Roussev, R.G., Barnea, E.R., Thomason, E.J., Coulam, C.B., 1994, *Clinical validation of preimplantation factor (PIF) assay*, Second World Conference on Preimplantation and Early Pregnancy in Humans, May, Atlantic City, NJ (abstract).

Roussev, R.G., Barnea, E.R., Thomason, E.J., Coulam, C.B., 1994, *A novel bioassay for detection of preimplantation factor (PIF)*, American Society of Reproductive Immunology, XVI Annual Meeting, June, Philadelphia, PA (abstract).

Coulam, C.B., Roussev, R.G., Thomason, E.J., Barnea, E.R., 1994, *Preimplantation factor (PIF) predicts subsequence pregnancy loss*, The American Fertility Society 50th Annual Meeting, November, San Antonio, TX (abstract).

Roussev, R.G., Goodman, C., Kaider, B.D., Barnea, E.R., Coulam, C.B., 1995, *Embryonic origin of preimplantation factor (PIF)*, Society for Gynecological Investigation 42nd Meeting, Chicago, IL (abstract).

Barnea, E.R., Roussev, R.G., Coulam, C.B., Leavis, P.C., 1996, *Partial characterization of embryo-derived preimplantation factor (PIF)*, Ninth World Congress on Human Reproduction, May, Philadelphia, PA (abstract).

Barnea, E.R., Leavis, P.C., Taliadouros, G.S., Levine, S.P., Barnea, J.D., Coulam, C.B., 1996, *Preimplantation factor (PIF): current developments*, Third World Conference on Early Pregnancy—An Interdisciplinary Approach, October, Atlantic City, NJ (abstract).

Barnea, E.R., Simon, J.H., Levine, S.P., Coulam, C.B., Taliadouros, G., Leavis, P.C., 1998, *Partial characterization of mammalian preimplantation factor (PIF) in culture and in vivo*, Fourth International Meeting Mechanisms in Local Immunity: and join meeting Fourth Meeting of Alps Adria Society for Immunology of Reproduction (AASIR), September, Opatija, Croatia (abstract).

Barnea, E.R., 1999, *Preimplantation Factor: A specific embryo viability factor*, The First National Congress on Human Assisted Reproduction with International Participation under the patronage of the Romanian Academy, Timisoara, Romania (abstract).

Gonzales, R.R., Leavis, P.C., Ramos, M.P., Coulam, C.B., Kolenko, V.M., Barnea, E.R., 2001, *Preimplantation factor (PIF) could be a portion of CD2 or a homologue peptide*, 57th Annual Meeting of the American Society for Reproductive Medicine, Orlando, FL (abstract).

Barnea, E.R., 2001, *Safeguards established at conception influence peri and postnatal life: Roles of Preimplantation Factor (PIF) and Developmental Proteins (DPs)*, World Congress of Perinatal Medicine, Parallel Scientific SIEP Meeting, Barcelona, Spain (abstract).

Barnea, E.R., 2002, *Novel Preimplantation Factors (PIF) and Developmental Peptides (DPs) are involved in safeguarding pregnancy*, The Fetus as a Patient, Budapest, Hungary (abstract).

Gonzales, R.R., Leavis, P.C., Albini, M.S., Paidas, M.J., Rivnay, B., Sathiyaseelan, T., Coulam, C.B., Barnea, E.R., 2002, *Preimplantation factors (PIF) embryo-derived immunomodulatory peptides: possible implications for maternal recognition and allograft tolerance*, 22nd Annual Meeting of the American Society for Reproductive Immunology, Chicago, IL (abstract).

Paidas, M., De-Hui Ku, Barnea, E.R., Gonzales, R., Arkel, Y., Rebarber, A., Lee, M.J., Mulholland, J., Urban, G., Lockwood, C., 2002, *Pregnancy Implantation Factor (PIF) activity is correlated with a pro-imflammatory response*, 23rd Annual Society for Maternal-Fetal Medicine Conference, San Francisco, CA (abstract).

Barnea, E.R., Lahijani, K.I., Roussev, R.G., Barnea, J.D., Coulam, C.B., 1994, *Further validation of an assay for preimplantation factor (PIF)*, Second World Conference on Preimplantation and Early Pregnancy in Humans, May, Atlantic City, NJ (abstract).

Gardner, DK, Lane, M, Kouridakis, K, Schoolvcraft, WB, *Complex physiologically based serum-free culture media increase mammalian embryo development*, in In vitro fertilization and assisted reproduction, Proc 10th World Congress. 1997: 187, Gomel, V, Leung, PCK, eds (abstract).

Barnea et al., *Preimplantation signaling by the embryo*, 3rd World Conference on Early Pregnancy, Oct. 3-6, 1996 (abstract).

R. Raghupathy, Immunol. Today 18, 478 (1997) (abstract).

T.G. Wegmann, H. Lin, L. Guilbert, T.R. Mosman, Immunol. Today 14, 353 (1993) (abstract).

A.C. Cavanagh, H. Morton, Eur. J. Biochem. 222, 551 (1994) (abstract).

M.P. Piccinni et al., Eur. J. Immunol., 8, 2431 (2001) (abstract).

S.N. Wickramasinghe, S.H. Abdalla, Baillieres Best. Pract. Res. Clin. Haematol. 13, 277 (2000) (abstract).

S. Romagnani, Annu. Rev. Immunol. 12, 227 (1994) (abstract).

G. Chaouat et al., Immunol. 154, 4261 (1995) (abstract).

H. Hong-Nerng et al., Fertil. Steril. 76, 797 (2001) (abstract).

M.Y. Wu et al., Am. J. Reprod. Immunol. 46,386 (2001) (abstract).

S.R. Choudhury, L.A. Knapp, Hum. Reprod. Update 7,113 (2001).

R.G. Roussev, E.R. Barnea, E.J. Thomason, C.B. Coulam, Am. J. Reprod. Immunol. 33, 68 (1995).

S. Heyner, Early Preg.3, 153 (1997).

A.K. Abbas, K.M. Murphy, A. Sher, Nature 383, 787 (1996).

G. Taubes, Science 290, 435 (2000).

Barnea, E.R., Policec, S., Checiu, M., Checiu, I., 2001, *Implantation*, in Obstetrics & Gynecology, Section 2 Human Re production—Anatomy, Physiology, Embryology, Munteanu Ed. (Romanian Academy of Science Publishers), pp. 117-123 (TOC only).

Barnea, E.R., Brusato, C.A., 2001, *Evolution of the feto-placental unit*, in Obstetrics & Gynecology, Section 2 Human Re production—Anatomy, Physiology, Embryology, Munteanu Ed. (Romanian Academy of Science Publishers), pp. 170-175.

Ancsin, et al., A Binding Site for Highly Sulfated Heparan Sulphate Is Identified in the N Terminus of the Circumsporozoite Protein, *J Biol Chem.* (May 21, 2004), 279(21):21824-21832.

Aplin, et al., Trophoblast-uterine interactions at implantation, *Reprod Biol and Endocrinol.* (Jul. 5, 2004), 2:48.

Barnea, et al., Embryo-derived Preimplantation Factor (PIF*): Methods to assess embryo viability towards successful pregnancy, Vth Indian Congress of Gynecologic Endoscopy and ART and SIEP, Khajuraho, India (Nov. 2004), (Abstract).

Barnea, et al., Expression of Novel Immunomodulators (PIF*) and Proliferation Controllers (DPs) by the Embryo and by the Placenta, Invited Speaker at the 32nd Conference of the European Teratology Society, Thessaloniki, Greece, Reproductive Toxicology (2004), 18:707-756 (Abstract.

Barnea, et al., Immune Modulation, by Embryo-Specific Peptides, Allow for Embryo Tolerance whilst Preserving the Maternal Host's Ability to Fight Pathogens: Preimplantation Factor (PIF), First Brown-Linkoping meeting on Basic and Clinical Aspects of Reproductive Immunology, Providence, RI (Nov. 15, 2002), (Abstract).

Barnea, et al., Novel Embryo-Derived Preimplantation Factor (PIF): An Immune-Modulatory Therapy Approach for Immune Disorders, 5th International Congress on Autoimmunity, Sorrento, Italy (2006).

Barnea, et al., Prediction of Implantation in ART using Molecular Biology, Assisted Reproductive Technology (2004), pp. 183-194.

Barnea, et al., Pregnancy derived compounds that control proliferation, Cancer and Pregnancy, Springer (Nov. 2000), 22:275-284.

Barnea, et al., Preimplantation Factor (PIF): Novel Immunemodulatory Peptide and Expression by Gestational Tissues, 12th International Federation of Placenta Association (IFPA), Kobe, Japan (Sep. 6-9, 2006), (Abstract).

Barnea, et al., Preimplantation Factor (PIF): Relevance for Human Pregnancy, 24th Ann. Mtg. of the American Society for Reproductive Immunology, St. Louis, MO (2004), (Abstract).

Barnea, et al., Preimplantation Factor: From Embryo Tolerance to Embryo Viability Detection and Treatment of Autoimmune Diseases, Eleventh International Symposium for Immunology of Reproduction. (ISIR) International House of Scientists, Varna, Bulgaria (2006).

Barnea, et al., The Embryo-Trophoblast Paradox, Embryonic Medicine and Therapy, Oxford University Press (1997), 15:256-279.

Barnea, Apply Embryo Derived Tolerance for Managing Reproductive and Immune Disorders: Preimplantation Factor (PIF), 27th Annual Meeting of the American Society for Reproductive Immunology, Toronto, Canada (2007), (Abstract).

Barnea, Critical Elements for Early Development and Beyond: Immune Tolerance (PIF) and Proliferation Control (DPs), Sixth World Conference of Early Pregnancy: Workshop on Embryology Early Pregnancy Investigation, Organized by SIEP, supported by Rotunda the Center for Human Reproduction and Mangeshikar Center for Gynaelogical Endoscopic Surgery, Jodphur, India (2002), (Abstract).

Barnea, Embryo-Maternal dialogue. Linking pregnancy recognition and proliferation control, 4th World Conference on Early Pregnancy, under the auspices of the Hungarian Society of Obstetrics and Gynecology and SIEP, the Society for the Investigation of Early Pregnancy, Pecs, Hungary (Jun. 1-3, 2000), (Abstract).

Barnea, Maternal Immune Recognition of Pregnancy is Initiated by Novel Embryo-Derived Preimplantation Factor (PIF), Invited Speaker. Hippokration Congress on Reproductive Immunology (4th ESRADI C) European Society for Reproductive and Developmental Immunology, Rhodes, Greece (2003), pp. 123-124 (Abstract 1.32)—Also pub. in J. Reprod. Immun. pp. 23-24.

Barnea, Signaling Between Embryo and Mother in Early Pregnancy: Basis for Development of Tolerance, Recurrent Pregnancy Loss Causes, Controversies and Treatment. Series in Maternal-Fetal Medicine, Informa Healthcare, Taylor and Francis Group publ. (2007), 2:15-22.

Barnea, et al., The epidemiology of cancer in pregnancy, Cancer and Pregnancy, Springer, London (2006), 1:1-6.

Bates, et al., Aberrant cytokine production by peripheral blood mononuclear cells in recurrent pregnancy loss?, *Hum Reprod.* (Sep. 2002), 17(9):2439-2444.

Database YbuOrit [Online], Nuclear receptor corepressor 2 (N-CoR2) (Silencing mediator of retinoic acid and thyroid hormone receptor) (SMRT) (SMRTe) (Thyroid-, retinoic-acid-receptor-associated corepressor) (T3 receptor-associating factor) (TRAC) (CTG repeat protein 26) (SMAP270), retrieved from EBI accession No. UNIPROT:Q9Y618 Database accession No. Q9Y618 (Nov. 1, 1999).

Gardner, et al., Culture of viable human blastocysts in defined sequential serum-free media, *Hum Reprod.* (Jun. 1998), 13(3):148-160.

Gonzalez, et al., Immunomodulatory features of preimplantation factors (PIF) from mouse embryos, 11th World Congress on Human Reproduction, Montreal, Canada (Jun. 1-4, 2002), (Abstract).

Medrano, et al., Sequence Analysis of the Polymerase Domain of HIV-1 Reverse Transcriptase in Naive and Zidovudine-Treated Individuals Reveals a Higher Polymorphism in $\alpha$-Helices as Compared with $\beta$-strands, *Virus Genes* (1999), 18(3):203-210 Also, *DATABASE UniProt [Online], Reverse transcriptase (Fragment), retrieved from EBI accession No. UNIPROT:Q9WFD3 Database accession No. Q9WFD3* (Nov. 1, 1999).

Mellor, et al., Extinguishing maternal immune responses during pregnancy: implications for immunosuppression, *Semin Immunol.* (Aug. 2001), 13(4):213-218.

Minhas, et al., Platelet Activating Factor and Conception, *Am J Reprod Immunol.* (Mar. 1996), 35(3):267-271.

Nahhas, et al., Early Pregnancy Factor (EPF) Determination in Pregnant and IVF/ET Patients, and in Human Embryo Cultures, American Fertility Society 15th Ann. Mtg., San Francisco, CA (1989), pp. S53-S54 (Abstract O-130).

Nahhas, et al., Human Embryonic Origin Early Pregnancy Factor Before and After Implantation, *Am J Reprod Immunol.* (Mar.-Apr. 1990), 22(3-4):105-108.

Paidas, et al., Preimplantation Factor (PIF) Upregulates First Trimester Toll Like Receptor-2, Supporting the Role of PIF as an Embryo Derived Factor Influencing Maternal Innate Immunity, 27th Annual Scientific Meeting of the Society for Maternal-Fetal Medicine, San Francisco, CA (Feb. 5-10, 2007), S140 (Abstract 448).

Park, et al., SMRTe, a silencing mediator for retinoid and thyroid hormone receptors-extended isoform that is more related to the nuclear receptor corepressor, *Proc Natl Acad Sci USA.* (Mar. 1999), 96(7):3519-3524.

Pinkas, et al., Immunosuppressive Activity in Culture Media Containing Oocytes Fertilized In Vitro, *Arch Androl.* (Jan.-Feb. 1992) 28(1):53-59.

Raghupathy, Pregnancy: success and failure within the Th1/Th2/Th3 paradigm, *Semin Immunol.* (Aug. 2001), 13(4):219-227.

Rogers, et al., Maternal-fetal tolerance is maintained despite transgene-driven trophoblast expression of MHC class I, and defects in Fas and its ligand, *Eur J Immunol.* (Nov. 1998), 28(11):3479-3487.

Rosario, et al., Morphological events in the primate endometrium in the presence of a preimplantation embryo, detected by the serum preimplantation factor bioassay, *Hum Reprod.* (Jan. 2005), 20(1):61-71.

Runmarker, et al., Pregnancy is associated with a lower risk of onset and a better diagnosis in multiple sclerosis, *Brain* (Feb. 1995), 118(1):253-261.

Sharma, et al., Genes regulating implantation and fetal development: a focus on mouse knockout models, *Front Biosci* (Sep. 1, 2006), 11:2123-2137.

Shi, et al., Sharp, an inducible cofactor that integrates nuclear receptor repression and activation, *Genes Dev.* (May 1, 2001), 15(9):1140-1151.

Shurtz-Swirski, et al., Anti-Cardiolipin Antibodies Affect Total and Pulsatile Placental Hcg Secretion During Early Pregnancy, Israel Conference of Fertility, Tel Aviv, Israel (1993), (Abstract).

Sipka, et al., Glucocorticosteroid dependent decrease in the activity of calcineurin in the peripheral blood mononuclear cells of patients with systemic lupus erythematosus, *Ann Rheum Dis.* (Apr. 2001), 60(4):380-384.

Somerset, et al., Normal human pregnancy is associated with an elevation in the human suppressive CD25+ CD4+ regulatory T-cell subset, *Immunology.* (May 2004), 112(1):38-43.

Szekeres-Bartho, Immunological Relationship Between the Mother and the Fetus, *Int Rev Immunol.* (Nov.-Dec. 2002), 21(6):471-495.

Than, et al., Embryo-Placento-Maternal Interaction and Biomarkers: From Diagnosis to Therapy-A Workshop Report, *Placenta* (Jan. 26, 2007), 28(Suppl. A)(21): S107-S110.

Barnea, From PIF identification to clinical applications: Immunemodulatory Embryo-Derived Novel Peptide: True BioMarker Dx and Nontoxic Rx Application, Mining the Plasma Proteone Meeting, Success Stories Session, PepTalk Conf., CHI Cambridge Healthtech Institute, Coronado, San Diego CA (Jan. 7-9, 2008) (Abstract).

\* cited by examiner (A) Fluorescence- labeled sPIF-1 binding to human Lymphocytes.
(B) Binding to the total PMBC population
(C) Binding to lymphocytes that form rosettes with platelets, P-L bioassay.

sPIF-1 BINDS MONOCYTES & MACROPHAGES
PRIMARY ANTIGEN PRESENTING CELLS AT BASAL STATE

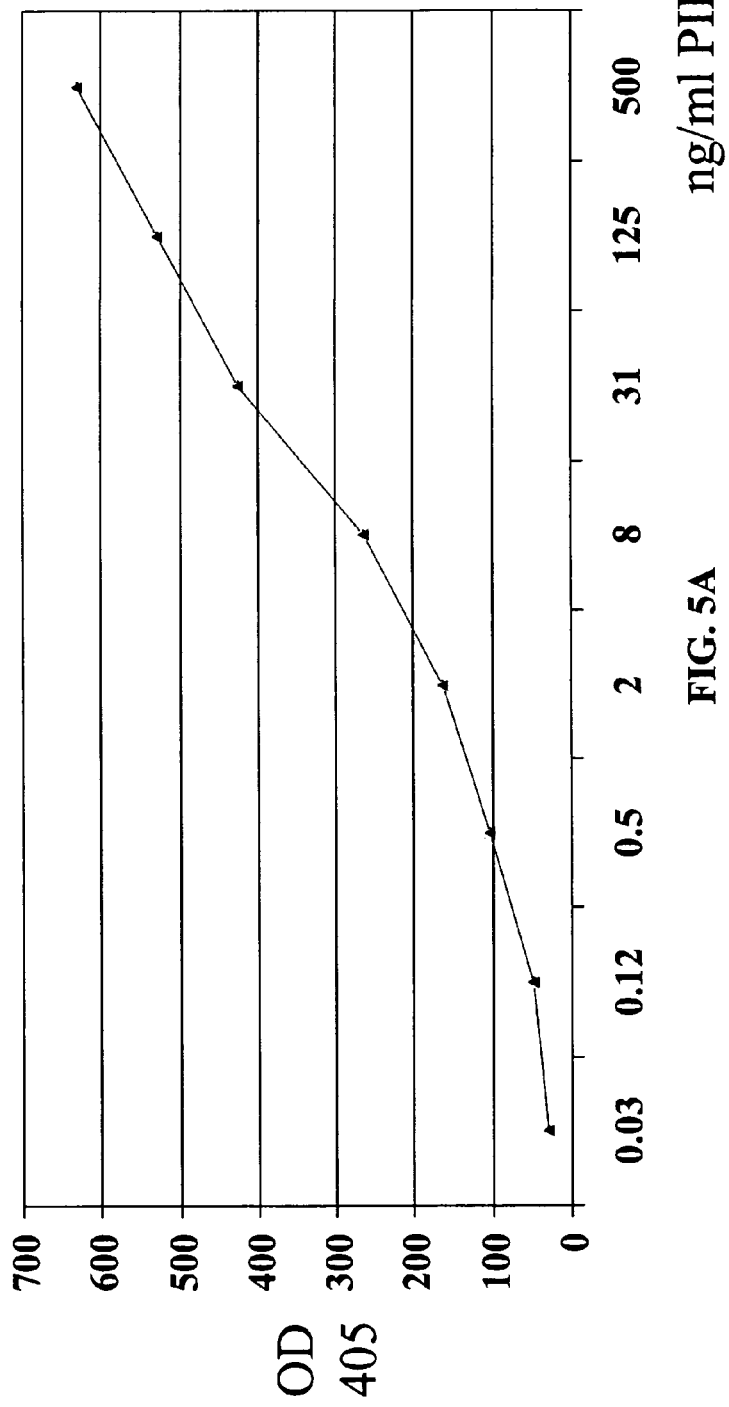

Direct ELISA Test. Peptide as test antigen. Affi-pure IgY as primary antibody and Goat anti-IgY-HRP as 2nd antibody. Fixed amount of antigen (5 ug/ml) and serial dilutions of IgY.

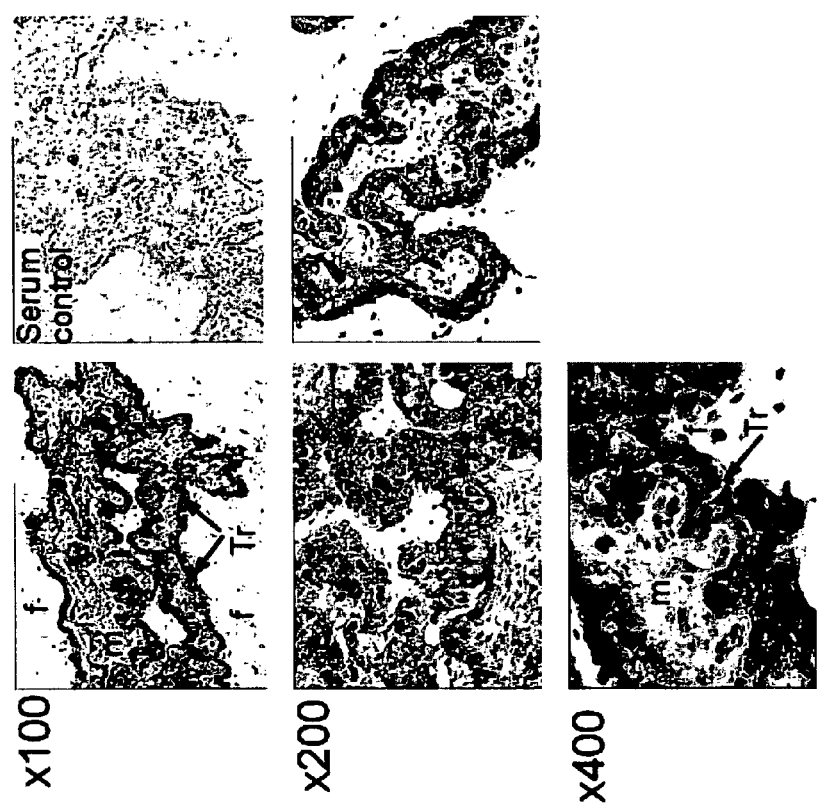

PIF-1, AND 3-LIKE PRO-PROTEINS Present in Human Term Placenta

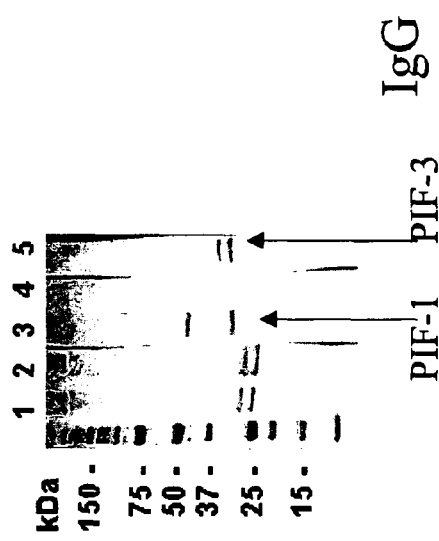

Western Blot Test Human placenta as test antigen. Lanes 1,3 – loaded 50 ug of Ag per lane, lanes 2,4,5 – loaded 100 ug of Ag per lane. Lanes 1,2 – incubated with affi-pure anti-Pif-1 IgY in 1:50 dilution, Goat anti-IgY-HRP dilution: 1:1000. Lane 3 – incubated with anti-Pif-1 Ab in 1:200 dilution, lane 4 – incubated with anti-Pif-2 Ab in 1:50 dilution, lane 5 – incubated with anti-Pif-3 Ab in 1:50 dilution, Goat anti-Rabbit –HRP dilution 1:1000. Colorimetric method for signal development.

FIG. 9

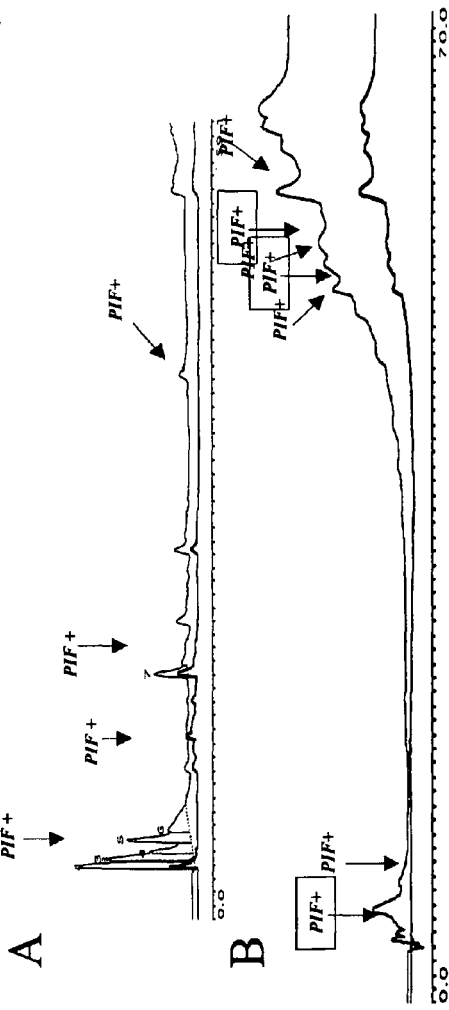
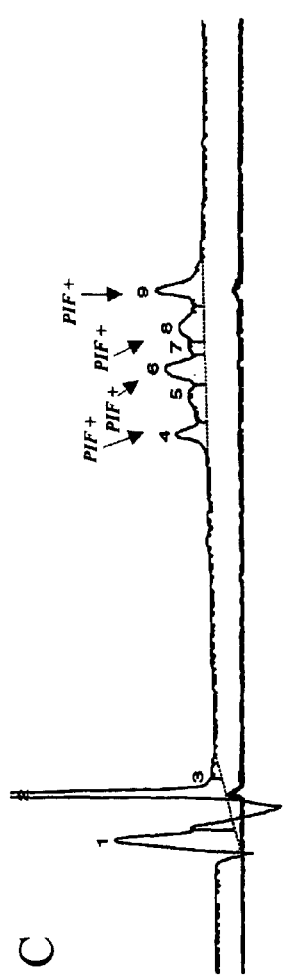
FIG. 10
A) HPLC profile of first trimester PPS in a preparative column. B) HPLC profile of PPS-3kDa previous purified by MabCD2 affinity chromatography C) HPLC profile of a PIF+ peak from PPS-3kDa previous purified by MabCD2 chromatography affinity and HPLC

PIF PRESENT IN HUMAN FETUS
IgG Staining
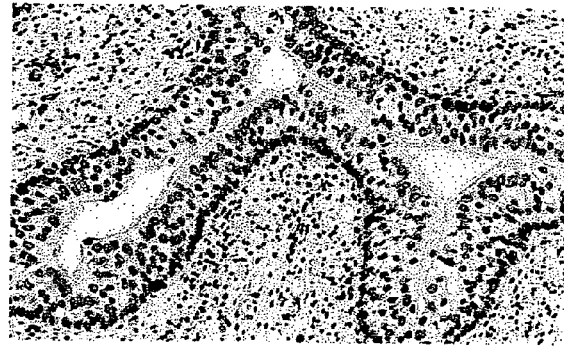
Spleen +4
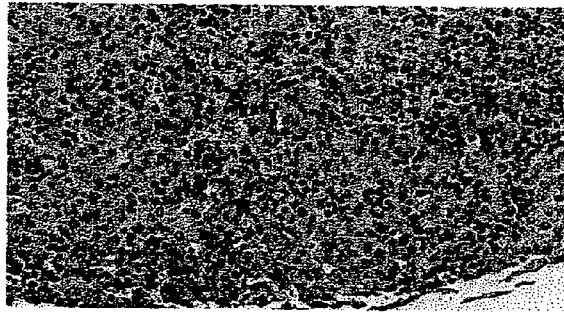
Liver +3
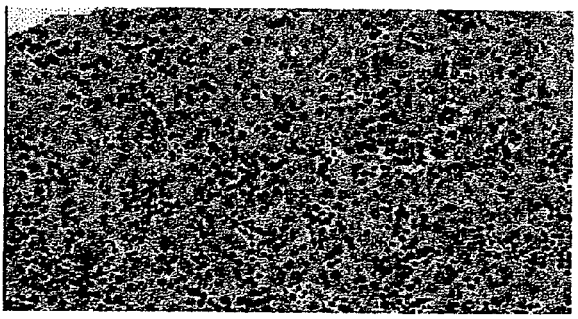
Esophagus 0
(+2) Adrenal, Stomach, Small Bowel, (+1) Thyroid, Other organs (0)
(14-18 weeks human fetus tissue array, IgG)
ProPREG, LLC
Proprietary Information
FIG. 13

METHODS OF ADMINISTERING PIF AGONIST PEPTIDES AND USES THEREOF

CROSS-REFERENCES TO RELATED APPLICATIONS

This application claims priority under 35 U.S.C. §119(e) from U.S. Provisional Application No. 60/513,370 filed Oct. 22, 2003, the contents of which are incorporated herein by reference in their entirety. This application is also a continuation-in-part application of U.S. Ser. No. 10/482,244 filed Aug. 11, 2004, now U.S. Pat. No. 7,273,708 dated Sep. 25, 2007, the contents of which are incorporated herein by reference in their entirety. U.S. Ser. No. 10/482,244 is a U.S. national phase application under 35 U.S.C. §371 of International Application No. PCT/US2002/020599 filed Jun. 28, 2002, which claims priority under 35 U.S.C. §119(a) from U.S. Provisional Application No. 60/302,607 filed Jul. 2, 2001.

BACKGROUND

Fertilization requires the proper interaction between the egg and sperm. Such a targeted event, even under natural conditions, is random, and hence the genetic make up of the nascent genome is unpredictable. The impending pregnancy has to prepare the maternal environment towards acceptance of a semi- or even a total allograft. This preparation can be divided to four distinct phases; the first is the pre-fertilization period, the second is the fertilization/post fertilization, the third phase is trophoblast development, and the final fourth phase is the implantation period.

The first phase, which is the pre-fertilization period, takes place during follicular development. The egg is surrounded by the cumulus oophorus and it is bathed in the rich follicular fluid. This fluid has some immune suppressive activity that may facilitate the fertilization process as well as post-fertilization development. This immune suppressive activity is required, due to the fact that shortly after fertilization, expression of foreign antigens, caused by the sperm, may be present. This mechanism, however, is not a necessary requirement. In cases of in vitro fertilization, no such fluid is available, and fertilization takes place without difficulty in an artificial environment. Moreover, women who have no ovaries can get pregnant by donor embryo transfer.

The next phase is the fertilization/post fertilization process. Once the sperm penetrates the egg it becomes "non visible" by the maternal environment. During the process of egg and sperm head fusion, as long as the egg surface membrane does not change its characteristics and become recognizable by the maternal immune system, no immune reaction would be expected. To safeguard the fertilized egg, it is rapidly surrounded by the zona pellucida, which is a hard and impenetrable shell designed to ward off immune cells. A further protection is due to the presence of the maternal cumulus cells. Those cells may further prevent direct access of immune cells to the embryo. The cumulus cells persist only for the first few days after fertilization because they facilitate the fallopian tube's cilia to propagate the zygote towards the uterus. Following fertilization, it is not excluded that small proteins derived from the maternal environment, such as cytokines, will reach the zygote and early embryo. So far, there has been no evidence for such an occurrence. Following the few initial embryonic cell divisions, to the eight-cell stage, the trophoblast phase is initiated.

The trophoblast phase that occurs by the sixteen-cell stage leads to embryoblast and trophoblast differentiation. While the trophoblast's genome is principally paternally derived, the embryoblast's genome is principally maternally derived. However, since the zona pellucida still surrounds the embryo, it provides a major protection against maternal immune onslaught. Therefore, it appears that the early embryo, during the pert-implantation phase, is rather well protected from maternal immune system. This is despite the fact that the embryo is a semi-antigen. This period in in vitro fertilization/embryo transfer (IVF/ET) procedures does not occur. Consequently, the development of maternal tolerance remains permissive until implantation, which is where direct embryo/maternal contact become a necessary prerequisite.

The final preparation phase is implantation, which occurs when the embryo reaches the uterus and intimate maternal contact is initiated. During implantation the zona pellucida opens, and the trophoblast cells are extruded. This is the time that the embryo is most vulnerable. The embryo is not yet attached to the maternal surface, and it is still exposed to endometrial maternal immune cells as well as potentially hostile cytokines. Of all phases of reproduction, the implantation phase is the most crucial. Specifically, in the case of embryo transfer, following IVF, the embryo has to sojourn in the endometrial cavity for 4-5 days until the maternal organism will accept it. This is a period of endometrial priming by embryonic signaling that leads to maternal tolerance, which is the pre-requisite for successful pregnancy.

Mammalian reproduction was the last to evolve and it required a major shift in the immune system. This is because it allowed a sperm, which might be regarded as a parasite, to invade the maternal organism, and impose, in part, its own genome expression. This suggests that the embryo must have an active role in allowing the initiation of pregnancy. This suggestion is supported by the following observations:

(i) Donor embryos can implant without difficulty, therefore sharing of maternal antigens is not required;

(ii) The site of embryo implantation is not obligatory, although the uterus is preferred. Occasionally, implantation can be found in the fallopian tubes, ovaries, and even inside the abdominal cavity;

(iii) Under certain circumstances, embryos from one species can be implanted and delivered by another species. Genetic mismatch also does not prevent a successful reproduction (i.e.: mule);

(iv) Only viable embryos will implant. Therefore, the implantation is an active act that requires a passive accommodation by the maternal recipient, upon which the embryo can impose its will, in order for the pregnancy to develop;

(v) Sick mammals can also get pregnant, which indicates that the maternal organism does not need to be in good health in order for pregnancy to initiate. This reiterates the passive role of the maternal organism and supports a specific embryo effect;

(vi) The chances of multiple embryos to implant are higher than that of a single embryo. Consequently, an enhanced embryo derived signaling is likely to lead to maternal acceptance; and (vii) Although a window of opportunity for implantation does exist, it is not strict. Therefore the embryo can implant in less than favorable endometrium, as well.

In conclusion, it appears that the embryo, to a large degree, controls it own destiny. This destiny is irrespective of timing in cycle, site of implantation, the sharing of genes, species, or the health of the mother.

Early work on pregnancy suggested that shortly after fertilization, certain changes that favor tolerance take place in the maternal environment. Those changes were believed to be due to early pregnancy factor (EPF) and platelet activating factor (PAF). However, these factors are not specific to pregnancy and are found in a non-pregnant state as well. More recent work indicates that the embryo's presence, and the products that it secretes, creates a favorable and tolerant environment for a successful pregnancy. Several reports have shown that the embryo-conditioned media has immune-modulatory effects on the maternal organism. The addition of the conditioned culture media, from human and mouse embryos, affects human immune cells activity. This immune modifying activity occurs very early, at the two-cell stage embryo. The activity is dependent on embryo viability, since the media of cultured atretic eggs does not exert such immune-modulatory features. Therefore, shortly after fertilization, the embryo starts actively to emit signals that create maternal recognition of pregnancy which lead to immune tolerance. The cumulus cells, which surround the segregated embryo, may serve as a relay system, since they contain active immune cells that secrete cytokines. Such an intimate contact between putative embryo-derived compounds, and the maternal immune system, would allow for a rapid diffusion of signals from the embryo. This would lead to a local immune response, due to the embryo presence, followed by a systemic maternal immune recognition. Such changes in maternal immunity are shown via a variety of bioassays, including a pre-implantation factor (PIF) assay that measures immune changes in the maternal systemic circulation. This immune change occurs within the first few days after fertilization. Additionally, using IVF cycles, it has been shown that within three days after embryo transfer, PIF activity can be found already in maternal circulation. This indicates that embryo-initiated signaling will rapidly create a systemic immune system tolerance to the embryo. Without wishing to be bound by theory, increased PIF activity may explain why implantation does not necessarily take place in the uterus, but it can occur elsewhere within the organism, and suggest that for embryo transfer to be successful, a similar PIF signal has to exist.

SUMMARY

Embodiments of the present invention relate to biological effects induced in vitro and/or in vivo by pre-implantation factor, (PIF), peptides, peptidomimetics, and compounds derived from pre-implantation embryos that harbors in part, is identical to, or is homologous to the amino acid sequence of PIF peptides or to the scrambled amino acid sequence of PIF peptides. The invention also relates to the development of antibodies to quantitatively detect PIFs peptides in biological fluids. In particular, the present invention relates to use of PIF peptides or peptidomimetics to effect changes on the immune system of a patient. More specifically, the addition of PIF peptides creates specific changes both in cellular immunity as well as in a patient's secreted cytokine profile. Namely, following exposure or stimulation to diverse mitogens, phytohemagglutinin (PHA), CD3 antibody, and the mixed lymphocyte reaction (MLR), PIF causes a shift towards immune tolerance reducing peripheral mononuclear blood cells (PBMC) proliferation while un-stimulated cells remain unresponsive to the effect of the PIF peptides. Moreover, addition of nPIF-$1_{15}$ (SEQ ID NO: 1) to stimulated PBMC caused an increase in $T_H2$ (IL10) type cytokine while reducing $T_H1$ (INF-γ) type cytokine secretion. Synthetic scrambled PIF peptide (scrPIF-$1_{15}$), (SEQ ID NO: 5), had no effect on these cells; while addition of synthetic PIF, sPIF-$1_{15}$ (SEQ ID NO: 13) together with the scrPIF-1 (SEQ ID NO: 5) blocked completely the effect of nPIF-$1_{15}$ (SEQ ID NO: 1) on the immune system.

Additional embodiments include peptides derived from pre-implantation embryos found in gestational biological fluids or tissues that have a PIF like activity and binds to PIF receptors on cell such as but not limited to monocytes, macrophages, as well as those that bind to activated lymphocytes.

Another embodiment of the present invention includes receptors expressed on the surface of cells which interact with the PIF peptides. These cells may be PBMC including T or B cells which appears in response to activation and responds to PIF peptides secreted by the embryo, they may include receptors on monocytes and macrophages that affect the cell biology of these cells upon interaction with embryo derived compounds or they may be receptors that transduce PIF effect on the immune system and elsewhere in the body.

The effects of PIF on the immune response may be measured using flow cytometry and ELISA techniques. Without wishing to be bound by theory, based on the use of fluorescence labeled PIF peptides, it is believed PIF binds to specific and likely novel cell surface receptor sites. These PIF receptors appear to be distributed on monocytes, >90% of B cells, and on 4% of un-stimulated and 80% of mitogen-stimulated T cells. Antibodies generated against PIF peptides can be used to develop ELISA and other assays to determine quantitatively or semi-quantitatively levels of PIF in biologic fluids. Any diagnostic procedure whereby compounds of pre-implantation embryo origin that decrease the $T_H1/T_H2$ ratio in lymphocytes are used to assess embryo quality in animals and humans. Such assays may be used as part of a diagnostic procedure whereby compounds of pre-implantation embryo origin that decrease the $T_H1/T_H2$ ratio in lymphocytes are used to assess the quality of pregnancy in animal and humans or to determine receptivity of the immune system and endometrium prior to pregnancy.

The present invention further relates to PIF peptides effect on endometrial cells leading to an increase in a major marker of endometrial receptivity, beta integrin, an adhesion molecule. The present invention further relates to generation of specific antibodies against the PIF by injecting KLH bound peptide and determining the titer of the antibody produced the basis for ELISA development. High titer polyclonal antibodies were generated against synthetic nPIF-$1_{15}$ (SEQ ID NO: 1), nPIF-$2_{13}$ (SEQ ID NO: 7) and nPIF-$3_{18}$ (SEQ ID NO: 10) and ELISA assays to measure PIF in biological fluids has been developed, showing differences between pregnant and non-pregnant samples for PIF-1 ELISA (SEQ ID NO: 1); determining presence of pregnancy, its viability and outcome in human as well as in other mammals.

PIF peptides and their receptors could be used beyond pregnancy for diagnostic and therapeutic uses. As a diagnostic, monitoring changes in the PIF receptor that are present on immune cells as well as elsewhere in the body. PIF receptor also could serve as an assay for PIF, where PIF would bind the receptor when present in biologic fluids to determine pregnancy and viability. In addition PIF peptides, since they modulate the immune system and do not cause basal immune suppression, could be applied to prevent transplant rejection. This is based on the observation that in the MLR system PIF-1 (SEQ ID NO: 1) blocked the reaction. This is viewed as an important assay in assessing tolerance development. Further the present invention relates to treatment of autoimmune diseases (including, but not limited to, lupus, arthritis, diabetes) where activated inappropriate immunity plays a key role. The ability to suppress that portion of the immune system that attacks various elements in the body may reduce or prevent these serious debilitating conditions.

In a further non-limiting embodiment, the present invention relates to the development of a novel non-steroid based contraceptive method, since PIF-1 (SEQ ID NO: 1) activity was blocked by scrPIF-1 (SEQ ID NO: 5) both on the immune cells and the endometrium, likely acting through the same receptor, since unlabeled scrPIF-1 (SEQ ID NO: 5) displaced FITC labeled PIF-1 (SEQ ID NO: 1) from the receptor. Therefore scrPIF-1 (SEQ ID NO: 5) could be administered to women or other mammals to prevent conception since it would not allow further embryo development, and will not interfere with the hormonal cycle. As such it could be devoid of the side effects that are associated with the use of current steroid based contraceptives. Data in vivo shows non toxic contraceptive effect of scrPIF-1. The scrPIF-1 (SEQ ID NO: 5), since it is an inducer of $T_H1$ activity, could have therapeutic use for stimulating the immune system in cases of immune suppression due to cancer, HIV for a non-limiting example. The present invention also relates to the use of PIF antibodies for immunocytochemical and Western blot to identify PIF related proteins in pregnant tissues, fetus and placenta. This allows identifying pregnancy pathologies like premature labor and growth restriction as non-limiting examples. The PIF antibodies used as affinity column can identify associated functional proteins in pregnant tissues as seen by identification of 10 distinct proteins in the term placenta, several of them novel for that tissue. In such embodiment, other biomarkers can be identified that may be modified by pregnancy disorders. Identification of these proteins allows the examination of the genes that are associated with these proteins highly relevant for blastocyst development. These proteins using mass spectrometry or antibodies can also aid together with PIF peptides to determine embryo viability following in vitro fertilization thereby increasing the chances for pregnancy following transfer.

DESCRIPTION OF THE DRAWINGS

In part, other aspects, features, benefits and advantages of the embodiments of the present invention will be apparent with regard to the following description, appended claims and accompanying drawings where:

FIG. 5A. $sPIF-1_{15}$ (SEQ ID NO: 13) ELISA standard curve PIF antibody detects low sPIF levels (pg). Polyclonal antibodies $AbPIF-1_{15}$ were generated against $sPIF-1_{15}$ (SEQ ID NO: 13) in rabbits (Covance Inc.). High titers 50% at 1:50,000 were achieved. Serial dilutions of synthetic $sPIF-1_{15}$ (SEQ ID NO: 13) were plated, blocked and then washed off. PIF-1 antibody (1:5000) was added incubated and washed off. Goat anti-rabbit antibody was added, incubated and washed off. Reaction was stopped by SDS and counted in plate reader (Biosynthesis Inc, G Vandydriff). The antibody affinity was also confirmed by using a competition analysis between biotin labeled and unlabeled $sPIF-1_{15}$ (SEQ ID NO: 13) (data not shown). Also, when scrPIF-1 (SEQ ID NO: 5) was tested in the assay the antibody did not recognize it attesting to the high specificity of the antibody that was generated. Similar dose dependent results in the ELISA were obtained with affinity purified PIF-2 and PIF-3 antibodies (dilutions of the antibody up to 25,600) with linearity to the 30 pM of the peptide.

FIG. 8. $nPIF-1_{15}$ (SEQ ID NO: 1) is present in the ovine placenta, as demonstrated by immunocytochemistry methods. $AbPIF-1_{15}$ was exposed to placental tissue derived from a midtrimester ovine fetus. Compared to the non specific staining by rabbit IgG, the PIF has show intense staining of the fetal portion of the placenta.

FIG. 9. Human term placental extracts were prepared (Dr Jerry Feitelson, GenWay, Inc) and were exposed to PIF antibodies using Western blot analysis, PIF like molecules were stained and the bands obtained were compared to a serial molecular weight standards run in parallel. Results showed that a number of PIF-1 related proteins are present at the 15-40 kDa range PIF-3 had a lower intensity with and was associated with different molecular weight bands. Finally, PIF-2 expression was minimal. This supports the notion that the human placenta may have precursor proteins from which by cleavage PIF peptides are produced. This also supports that view that PIF like molecules are present throughout pregnancy. Finally, it documents that in terms of intensity of expression in human by far PIF-1 is the most relevant at term.

FIG. 10. PIF purification from pregnant porcine serum (PPS). A) HPLC profile of first trimester PPS in a preparative column. B) HPLC profile of PPS-3 kDa previously purified by MabCD2 affinity chromatography. C) HPLC profile of a PIF+peak from PPS-3 kDa previous purified by MabCD2 chromatography affinity and HPLC.

FIG. 13 reflects expression of PIF in various human tissues using IgG in 14-18 weeks human fetus tissue array.

DETAILED DESCRIPTION

Figure 1:
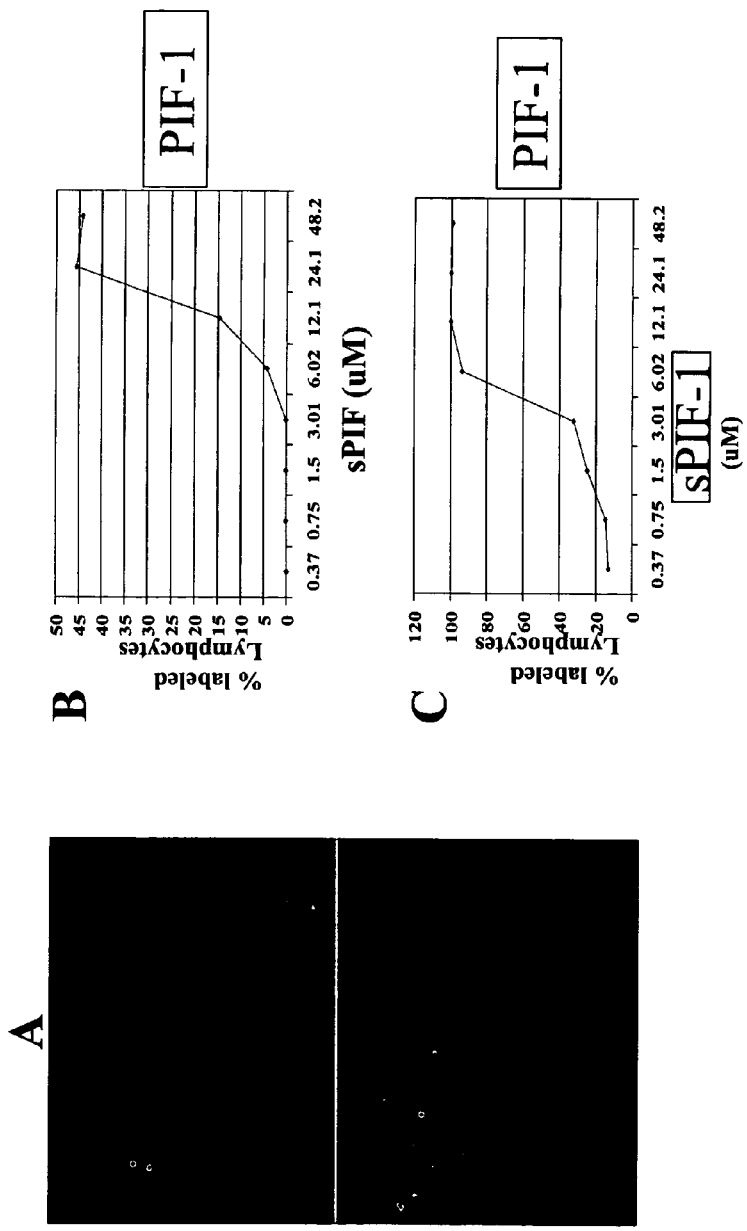
FIG. 1 shows that $sPIF-1_{15}$ (SEQ ID NO: 13), binds to PBMC, which forms rosettes in their P-L assay. (A) Fluorescence-labeled $sPIF-1_{15}$ (SEQ ID NO: 13), binding to human Lymphocytes in a dose dependent manner. (B) Binding of FITC $sPIF-1_{15}$ (SEQ ID NO: 13), to the total PBMC population (C) Binding to lymphocytes that form rosettes with platelets, P-L bioassay, documents presence of $nPIF-1_{15}$ (SEQ ID NO: 1), receptors on the PBMC surface FIG. 2A. $sPIF-1_{15}$ (SEQ ID NO: 13) increases the percentage of PBMC that contain $T_H2$ type cytokines (IL 10, IL 4 while $scrPIF-1_{15}$ (SEQ ID NO: 5) has a $T_H1$ bias (INF-gamma). Isolated PBMC were stimulated by PHA (1 ug/ml) and cultured 2-4 days with $sPIF-1_{15}$ (SEQ ID NO: 13) or $scrPIF-1_{15}$ (SEQ ID NO: 5) 30 nM. PBMC cytokines content was determined by specific staining using flow cytometry.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

In one embodiment, the PIF peptides of the invention are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7 membered alkyl, amide, amide lower alkyl, amide di(lower alkyl), lower alkoxy, hydroxy, carboxy and the lower ester derivatives thereof, and with 4-, 5-, 6-, to 7 membered heterocyclics. For example, proline analogs can be made in which the ring size of the proline residue is changed from 5 members to 4, 6, or 7 members. Cyclic groups can be saturated or unsaturated, and if unsaturated, can be aromatic or nonaromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, Ann. Rep. Med. Chem. 24, 243-252, 1989). Certain peptidomimetic compounds are based upon the amino acid sequence of the peptides of the invention. Often, peptidomimetic compounds are synthetic compounds having a three-dimensional structure (i.e. a "peptide motif") based upon the three-dimensional structure of a selected peptide. The peptide motif provides the peptidomimetic compound with the desired biological activity, i.e., binding to PIF receptors, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, Curr. Op. Chem. Biol. 2, 441-452, 1998; Hruby et al., Curr. Op. Chem. Biol. 1, 114-119, 1997; Hruby & Balse, Curr. Med. Chem. 9, 945-970, 2000). One class of peptidomimetics a backbone that is partially or completely non-peptide, but mimics the peptide backbone atom-for atom and comprises side groups that likewise mimic the functionality of the side groups of the native amino acid residues. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

The PIF assay; as disclosed in U.S. Pat. No. 5,646,003 to Barnea et al., entitled "Preimplantation Factor" issued Jul. 9, 1997, and in U.S. Pat. No. 5,981,198 to Barnea et al., entitled "Preimplantation Factor" granted Nov. 9, 1999, the disclosures of which are incorporated herein by reference in their entirety, may be used to measure the response of the immune system to pregnancy specific preimplantation factors. Studies employing the PIF assay for culture media of human or mouse embryos that were grown, show that PIFs were able to increase the in-vitro formation of rosettes between donor lymphocytes and platelets in the presence of monoclonal anti-CD2 (type T11-1). Lymphocyte-platelet rosettes result from the interaction of the T cell surface protein CD2 with its ligand CD58 expressed on the platelet membrane. Anti-CD2, by binding to the CD2 antigen on the T cells, inhibits their interaction with platelets. However, the embryo-derived factor(s), PIFs, present in the culture medium or pregnant peripheral sera appears to counteract this inhibition. The PIF activity was already apparent in the viable two-cell stage embryo. Thus both of those compounds properties are very likely to be similar. This observation strongly suggests that there are several putative compounds that may be very potent, and create an environment that is favorable for pregnancy.

Using this assay, it has been determined that the presence of PIF activity in maternal serum within four days after embryo transfer indicates a >70% chance of successful pregnancy outcome. In contrast, absence of PIF activity indicated that pregnancy would not develop in 97% of cases. PIF is detectable 5-6 days after intrauterine insemination and is absent in non-pregnant serum and in culture media of non viable embryos, present in the sera of various mammals including horse, cow, pig and humans. Without wishing to be bound by theory, the PIF assay results indicate that if the embryo is able to secrete these immunomodulatory PIF compounds, it is capable of implanting and achieving a good pregnancy outcome. The importance of PIF as a marker of a good quality pregnancy is further illustrated by the fact that if a pregnancy ends in miscarriage, the PIF activity progressively declines until it reaches non-detectable levels. In contrast, in the case of a poor quality pregnancy, Human Chronic Gonadotropin (hCG) levels do not change significantly for the next 3 weeks until the miscarriage is clinically evident.

PIF activity is found in several mammalian species, including humans, horse, cow, pig, and mouse and sheep. Human immune cells used for the PIF assay (homologous lymphocytes and platelets) interacted well with the human sera, as well as with sera from different species and embryo culture media. This cross-species interaction indicates that similar compounds are involved in the different species. PIF activity is due to the presence of similar low molecular weight peptides, both in mouse embryo culture media and in pregnant porcine serum. A PIF assay was used as a test to identify and characterize the PIF related compounds within a conditioned mouse embryo culture media. Using a multi-step chromatographic technique, coupled with the PIF bioassay, a group of a putative PIF embryo derived peptides with 9-18 amino acids in length were identified and sequenced. These sequences are disclosed in PCT/US02/20599 to Barnea et al., entitled "New Assays for Preimplantation Factor and Preimplantation Peptides," filed Jun. 28, 2002, the contents of which are incorporated herein by reference in their entirety. Based on the sequences derived, synthetic peptides were generated.

The first natural PIF compound identified, termed $nPIF-1_{15}$ (SEQ ID NO: 1), is a 15 amino acid peptide. A synthetic version of this peptide, $sPIF-1_{15}$ (SEQ ID NO: 13), showed activity that was similar to the native peptide, $nPIF-1_{15}$ (SEQ ID NO: 1). This peptide is homologous to a small region of the Circumsporozoite protein, a malaria parasite. The second PIF peptide, $nPIF-2_{13}$ (SEQ ID NO: 7), includes 13 amino acids and shares homology with a short portion of a large protein named thyroid and retinoic acid transcription co-repressor, which is identified as a receptor-interacting factor, (SMRT); the synthetic version is sPIF-2 (SEQ ID NO: 14). The third distinct peptide, $nPIF-3_{18}$ (SEQ ID NO: 10), consists of 18 amino acids and matches a small portion of reverse transcriptase; the synthetic version of this peptide $sPIF-3_{18}$ is (SEQ ID NO: 15). $nPIF-4_9$ (SEQ ID NO: 12) shares homology with a small portion of reverse transcriptase.

A composition comprising a synthetic PIF peptide and an excipient. In further embodiments, the synthetic PIF peptide corresponds to the amino acid sequence of SEQ ID NO: 1, SEQ ID NO: 2, SEQ ID NO: 3, SEQ ID NO: 4, SEQ ID NO: 6, SEQ ID NO: 7, SEQ ID NO: 10, or SEQ ID NO: 12 or comprises the amino acid sequence of SEQ ID NO: 13, SEQ ID NO: 14, SEQ ID NO: 15, SEQ ID NO: 16, or SEQ ID NO: 17 or a peptidomimetic thereof. In another embodiment, the composition may further include a cell having an expressed PIF receptor bonded to said PIF peptide, for example, embryo cells.

In a further embodiment a compound of the formula $R_1-R_2-R_3-R_4-R_5-R_6-R_7-R_8-R_9-R_{10}-R_{11}-R_{12}-R_{13}-R_{14}-R_{15}$, wherein $R_1$ is Met or a mimetic of Met, $R_2$ is Val or a mimetic of Val, $R_3$ is Arg or a mimetic of Arg, $R_4$ is Ile or a mimetic of Ile, $R_5$ is Lys or a mimetic of Lys, $R_6$ is Pro or a mimetic of Pro, $R_7$ is Gly or a mimetic of Gly, $R_8$ is Ser or a mimetic of Ser, $R_9$ is Ala or a mimetic of Ala, $R_{10}$ is Asn or a mimetic of Asn, $R_{11}$ is Lys or a mimetic of Lys, $R_{12}$ is Pro or a mimetic of Pro, $R_{13}$ is Ser or a mimetic of Ser, $R_{14}$ is Asp or a mimetic of Asp and $R_{15}$ is Asp or a mimetic of Asp is provided. In a further embodiment, a compound comprising the formula $R_1-R_2-R_3-R_4-R_5-R_6-R_7-R_8-R_9-R_{10}$, wherein $R_1$ is Ser or a mimetic of Ser, $R_2$ is Gln or a mimetic of Gln, $R_3$ is Ala or a mimetic of Ala, $R_4$ is Val or a mimetic of Val, $R_5$ is Gln or a mimetic of Gln, $R_6$ is Glu or a mimetic of Glu, $R_7$ is H is or a mimetic of H is, $R_8$ is Ala or a mimetic of Ala, $R_9$ is Ser or a mimetic of Ser, and $R_{10}$ is Thr or a mimetic of Thr; a compound comprising the formula $R_1-R_2-R_3-R_4-R_5-R_6-R_7-R_8-R_9-R_{10}-R_{11}-R_{12}-R_{13}-R_{14}-R_{15}-R_{16}-R_{17}-R_{18}$, wherein $R_1$ is Ser or a mimetic of Ser, $R_2$ is Gly or a mimetic of Gly, $R_3$ is Ile or a mimetic of Ile, $R_4$ is Val or a mimetic of Val, $R_5$ is Ile or a mimetic of Ile, $R_6$ is Tyr or a mimetic of Tyr, $R_7$ is Gln or a mimetic of Gln, $R_8$ is Tyr or a mimetic of Tyr, $R_9$ is Met or a mimetic of Met, $R_{10}$ is Asp or a mimetic of Asp, $R_{11}$ is Asp or a mimetic of Asp, $R_{12}$ is Arg or a mimetic of Arg, $R_{13}$ is Tyr or a mimetic of Tyr, $R_{14}$ is Val or a mimetic of Val, $R_{15}$ is Gly or a mimetic of Gly, $R_{16}$ is Ser or a mimetic of Ser, $R_{17}$ is Asp or a mimetic of Asp and $R_{18}$ is Leu or a mimetic of Leu; and a compound comprising the formula $R_1-R_2-R_3-R_4-R_5-R_6-R_7-R_8-R_9$, wherein $R_1$ is Val or a mimetic of Val, $R_2$ is Ile or a mimetic of Ile, $R_3$ is Ile or a mimetic of Ile, $R_4$ is Ile or a mimetic of Ile, $R_5$ is Ala or a mimetic of Ala, $R_6$ is Gln or a mimetic of Gln, $R_7$ is Tyr or a mimetic of Tyr, $R_8$ is Met or a mimetic of Met, and $R_9$ is Asp or a mimetic of Asp is provided.

Without wishing to be bound by theory, present evidence suggests that both within the embryos immediately surrounding (found in the fallopian tube, and endometrium in vivo), and in the peripheral circulation, similar PIF peptides may be responsible for both the immune effects, and for the creation of a pro-pregnancy environment.

Considerable evidence exists that impaired maternal immune tolerance to the semi-allogeneic conceptus is a cause of implantation failure and pregnancy loss. The distribution of T-helper cell ($T_H$) sub-populations and the resulting local and systemic cytokine balance may play an important role in pregnancy viability. Following antigenic stimulation, $T_H$ cells respond by differentiating into one of two cell types: $T_H1$ which produces mainly interleukin 2 (IL-2) and interferon γ (IFN-γ) as well as tumor necrosis factor α (TNF-α); and $T_H2$, which produces IL-4, IL-5 and IL-10. $T_H$-specific cytokines tend to both stimulate proliferation of the $T_H$ cell subset from which they are derived and inhibit development of the opposite $T_H$ cell subset. $T_H1$ cells are involved in cell-mediated immune reactions while $T_H2$ cells are involved in humoral immunity. A predominance of $T_H2$ cytokines is found in normal pregnancies, and IL-4 and IL-10 released by these cells appear to support pregnancy. In contrast, the $T_H1$ cytokines, IL2, IFN-γ and TNF-α are associated with reproductive failure in both humans and mice. However both types of cytokines are required to maintain pregnancy, since the maternal system must be able to fight against infection while tolerating the fetus. It has been postulated that the pre-implantation embryo may play a role in protecting itself from maternal immune rejection by secretion of factors that would promote the shift of $T_H$ cells towards the $T_H2$ phenotype. These PIF compounds may be to be used for treatment of inflammatory or other immunological diseases, and preferably the drug or biological is derived from- or its structure is based on the structure of the circumsporosoite protein of malaria.

In one embodiment, embryo-derived compounds, PIF peptides or peptidomimetics thereof, can be used for both diagnosis and therapy. Non-limiting examples of the effects of such PIF peptides include modulation of the immune system while not causing basal immune suppression, and use of PIF peptide to enhance endometrial receptivity. Such methods of treatment may involve increased expression of endometrial receptivity markers, including, but not limited to beta 3-integrin.

In another embodiment, a method of detecting a PIF petptide is provided. The PIF peptide may include, for example, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17. In a further embodiment, a method of detecting a PIF peptide which includes a fragment of nPIF-$1_{15}$, nPIF-$2_{13}$, nPIF-$3_{18}$ or nPIF-$4_9$.

PIF peptides and peptidemimetics of the present invention may be coupled to produce labeled peptides, for example but not limited to FITC, biotin, rhodamine, radioactive labels, fluorescent nanocrystals, and other labels known to those skilled in the art, that may be used to identify PIF receptor sites present on immune cells, endometrium, on the embryo itself, as well as elsewhere within the body where PIF peptides specifically bind.

Embodiments of the present invention may be used to identify and clone the genes that are responsible for PIF peptides expression. cDNA library is prepared from human placenta (Invitrogen) that have libraries of 1-2.5 kb size inserts which represent even the rarest sequences. Oligonucleotides are generated based on the peptides sequences and are probed against the cDNA library using plate screening procedures. The PIF peptide presence in the placenta was adding previously documented using immunohistochemical techniques by labeled PIF-1 antibody. The species of PIF peptides present in the placenta are confirmed with affinity purified and labeled PIF-1, PIF-2, and PIF-3 antibodies using a Western blot. The present invention may be used to generate specific antibodies polyclonal and monoclonal for assay development to measure PIF levels and activity in biologic fluids and tissues such as but not limited to serum, blood, urine, milk, and saliva as well as embryo culture media, gestational tissue, and fetal tissue.

Embodiments of the present invention include those peptides derived from pre-implantation embryos that induces $T_H2$ type cytokines like IL-10 synthesis or secretion from lymphocytes or other white blood cells and pharmacophores that binds specifically to PIF receptors (such but not limited to (A)VRIKPGSANKPSDD or (O)VRIKPGSANKPSDD) or by substituting with L amino acids or by adding PEG. Preferably such peptides are from pre-implantation embryos and increases $T_H2/T_H1$ ratio through increased number of lymphocytes containing the desired cytokines and or by preferential secretion or $T_H2$ over $T_H1$ cytokines into the media. Such pre-implantation embryo-derived peptide may be used to cause a shift from pro-inflammatory to anti-inflammatory activities in lymphocytes.

In a further embodiment isolated or synthetic PIF peptides may be used in a method of identifying cellular or tissue binding sites for PIF peptides in a patient, the method comprising administering labeled PIF peptides to said tissue and detecting the label. The binding sites may include, for example, immune cells, endometrial cells, epithelial cells, gestational tissues, embryos and the like.

In another embodiment, a method of identifying PIF receptors on cells is provided. The method may involve combining labeled PIF peptides with activated immune cells membranes and further detecting the presence of labeled PIF peptides on activated cells.

PIF peptides or peptidomimetics may be used to treat a patient by administering to the mother a therapeutic amount of one or more PIFs to create tolerance for the embryo and therefore pregnancy acceptance by the mother. In this embodiment PIF peptides can be used for the treatment of infertility disorders and for the enhancement of pregnancy. Other non-limiting examples where such PIFs may be used include preventing miscarriage and premature labor in mammals such as women, farm, and non-farm animals. The PIF peptides, peptidomimetics or compositions thereof may be administered using transdermal methods including patch, by injection, or pill, and may include liposome or carbohydrate coated formulations, for example.

In another non-limiting embodiment PIF peptide could be added to embryo culture media in order to enhance the ability of the transferred embryos to implant thereby reducing the number of embryos that are needed in order to have a high rate of implantation, and successful pregnancy. PIF could also enhance embryonal viability by acting in an autocrine manner on the embryo itself.

In further embodiments, methods of involving compounds of pre-implantation embryo origin that decrease the $T_H1/T_H2$ ratio are used as drugs (biologics) to improve the immune system of the mother to be able to better receive the embryo, as a treatment of infertile women (parenterally or as a co-additive to the embryo cultures in the ET procedure) are provided.

Pre-implantation embryo origin compounds or analogs may be used in procedures that decrease the $T_H1/T_H2$ ratio in lymphocytes. In these procedures the PIFs are used as drugs or biologics to treat immunological diseases that benefit from a reduction in the pro-inflammatory activity or enhancement of anti inflammatory activity of the immune system in animals and humans. Alternatively, these compounds and their analogs can block a decrease in the $T_H1/T_H2$ ratio in lymphocytes in which case they are used as drugs or biologics to treat immunological diseases where antibodies are over-produced and inhibition thereof is beneficial in humans and animals. For example, PIF peptides or peptidomimetics may be administered to non-pregnant patients that have autoimmune diseases like lupus and rheumatoid arthritis where the aim is to reduce the rate of activated immunity while maintaining the basal immunity that is required for defense of the organism. In another example, the compounds of pre-implantation embryo origin are used to decrease the $T_H1/T_H2$ ratio in lymphocytes are used to control the function of other proteins that do same effects (e.g. Progesterone Induced Blocking Factor). The administration can be made through non-limiting examples such as a patch, injection, or pill form.

The PIFs may have their molecular structure and/or of amino acid sequence modified to form antagonists. In one embodiment, PIF antagonists may include scrambled PIF peptides, including SEQ ID NO: 5, SEQ ID NO: 8 and SEQ ID NO: 9. In a further embodiment, compositions comprising a scrambled PIF peptide that blocks PIF recognition by cell receptors and an excipient are provided. The composition may further include a cell having an expressed PIF receptor bonded to the scrambled PIF peptide.

Another embodiment of the invention is the use of scrambled PIFs, including but not limited to scrPIF-$1_{15}$ (SEQ ID NO: 5), to antagonize endogenous PIF pro-fertility effect, thereby preventing pregnancy initiation thus serving as a contraceptive for mammals including women. The scrPIF-$1_{15}$ (SEQ ID NO: 5) administration can be made through a non-limiting example, a patch, injection or in a pill form. Another non-limiting application may be administration of scrPIF-$1_{15}$ (SEQ ID NO: 5) at term to induce labor. Modified PIF peptides may also be used to negates PIF activity on any cell, tissues and exert contraceptive effects, or lead to premature delivery, or induce delivery. Any procedure whereby compounds of pre-implantation embryo origin that decrease the $T_H1/T_H2$ ratio in lymphocytes are used as drugs or biologics to prepare the endometrium (uterus) to maintain a healthy implantation window by inducing implantation window specific gene product(s) expression.

Another embodiment of the present invention provides for a method of identifying the site of action, the cell receptors, to which PIF peptides have to bind in order to exert their biological effects. This binding may be on immune cells, endometrium, and elsewhere in the organism, including the embryo itself. The method may include administering a labeled PIF peptide and further detecting the labeled PIF peptide. Further embodiments provide for a composition for identifying PIF receptor sites comprising a PIF peptide and a label. The label may include, for example, FITC, biotin, rhodamine, radioactive isotopes and fluorescent labels, such as nanocrystals. A further embodiment includes isolation and cloning of these receptors. cDNA library of PBMC (Invitrogen) is used for expression screening. Binding of PIF-1,2,3 (FITC) to COS-M6 cells is examined and positive clones are sequenced. This method also provides for identifying the intracellular mechanisms including the transcription factors that lead to the changes noted in cytokines secretion but not limited to the immune system's function. Also the method allows for the identification of the secretory products, such as but not limited to cytokines, and growth factors, that are modified following exposure to the PIF peptides. It also provides the method for identifying the genes' expression that is modified secondary to PIF peptides' effect.

Another embodiment of the present invention provides for making polyclonal or monoclonal antibodies that were raised against PIF. In one non-limiting embodiment, polyclonal or monoclonal antibodies may be raised against PIF in mice and rabbits. In another embodiment, antibodies to PIF may be created by providing a hybridoma cell that produces a monoclonal antibody specific for a PIF peptide and culturing the cell.

Such antibodies provide a method for determining the presence of PIF levels in samples by using but not limited to ELISA, EIA, lateral flow assay, microfluidics or mass spectometry. Such a method and antibodies may allow precise measurements of PIF levels in fluids such as but not limited to maternal blood, urine, saliva, milk, and embryo culture media and gestational tissues. The method is applicable for all PIF peptides and may be used to provide an early diagnostic method that reflects pregnancy and its viability in various patients starting at the pre-implantation period. The patients may include women, to monitor results of infertility therapy and pregnancy well being, as well as other mammals, including farm and non-farm animals, and non-mammals. In the embryo culture media the ELISA assay using such antibodies provides a method for assessing the presence of PIF peptides to assess embryo viability before transfer. Various aspects of the present invention will be illustrated with reference to the following non-limiting examples.

TABLE 1

PIF Peptides

| (SEQ ID NO) | Peptide | Amino Acid Sequence |
| --- | --- | --- |
| SEQ ID NO: 1 isolated native, matches region of Circumsporozoite protein (Malaria) | nPIF-$1_{15}$ | MVRIKPGSANKPSDD |
| SEQ ID NO: 2 isolated native, matches region of Circumsporozoite protein (Malaria) | nPIF-$1_{(15-alter)}$ | MVRIKYGSYNNKPSD |
| SEQ ID NO: 3 isolated native, matches region of Circumsporozoite protein (Malaria) | nPIF-$1_{13}$ | MVRIKPGSANKPS |
| SEQ ID NO: 4 isolated native, matches region of Circumsporozoite protein (Malaria) | nPIF-$1_9$ | MVRIKPGSA |
| SEQ ID NO: 5 synthetic, scrambled amino acid sequence from region of Circumsporozoite protein Malaria | scrPIF-$1_{15}$ | GRVDPSNKSMPKDIA |
| SEQ ID NO: 6 isolated native, matches region of human retinoid and thyroid hormone receptor-SMRT | nPIF-$2_{10}$ | SQAVQEHAST |
| SEQ ID NO: 7 isolated native, matches region of human retinoid and thyroid hormone receptor (SMRT) | nPIF-$2_{13}$ | SQAVQEHASTNMG |

TABLE 1-continued

PIF Peptides

| (SEQ ID NO) | Peptide | Amino Acid Sequence |
|---|---|---|
| SEQ ID NO: 8<br>synthetic, scrambled amino acid sequence from region of human retinoid and thyroid hormone receptor SMRT | scrPIF-2$_{13}$ | EVAQHSQASTMNG |
| SEQ ID NO: 9 | scrPIF-2$_{14}$ | GQASSAQMNSTGVH |
| SEQ ID NO: 10<br>isolated native, matches region of Rev Trans | nPIF-3$_{18}$ | SGIVIYQYMDDRYVGSDL |
| SEQ ID NO: 11<br>synthetic, scrambled amino acid sequence from region of Circumsporozoite protein Malaria | Neg control for negPIF-1$_{15}$ | GMRELQRSANK |
| SEQ ID NO: 12<br>isolated native, matches region of Rev Trans | nPIF-4$_9$ | VIIIAQYMD |
| antibody of native isolated nPIF-1$_{15}$ | AbPIF-1$_{15}$ | |
| (SEQ ID NO: 13)<br>synthetic, amino acid sequence from region of Circumsporozoite protein Malaria | sPIF-1$_{15}$ | MVRIKPGSANKPSDD |
| (SEQ ID NO: 14)<br>synthetic, amino acid sequence from of human retinoid and thyroid hormone receptor SMRT | sPIF-2$_{13}$ | SQAVQEHASTNMG |
| (SEQ ID NO: 15)<br>synthetic, amino acid sequence from region of Circumsporozoite protein Malaria | sPIF-3$_{18}$ | SGIVIYQYMDDRYVGSDL |
| (SEQ ID NO: 16)<br>synthetic, amino acid sequence from region of Circumsporozoite protein Malaria | sPIF-1$_9$ | MVRIKPGSA |
| antibody of native isolated nPIF-2$_{(13)}$ | AbPIF-2$_{13}$ | |
| antibody of native isolated nPIF-3$_{(18)}$ | AbPIF-3$_{18}$ | |
| (SEQ ID NO: 17)<br>synthetic | sPIF-4$_9$ | VIIIAQYMD | n=native, s=synthetic, scr=scrambled, same AA, ( )=number of AA, AII=antibody

Example Biological Effects of PIF Peptides

Preimplantion factor peptides were synthesized by solid-phase peptide synthesis (SPPS, Applied Biosystems Peptide Synthesizer, Model 433) employing Fmoc (9-fluorenyl-methoxycarbonyl) chemistry in which the α-amino nitrogen of each amino acid is blocked with Fmoc. Upon completion of the synthesis, final purification is carried out by reversed-phase HPLC and identity is verified by MALDI-TOF mass spectrometry and amino acid analysis. sPIF-1$_{15}$ (SEQ ID NO: 13) and scrPIF-1$_{15}$ (SEQ ID NO: 5) scrambled peptide (GRVDPSNKSMPKDIA) and an irrelevant 11 amino acid negative control peptide negPIF-1$_{15}$ (SEQ ID NO: 11) (GM-RELQRSANK) containing a similar carboxyl-terminal sequence, were synthesized. Peptides were labeled on their N-termini with fluorescein isothyocyanate (FITC) in the solid phase. A spacer group (b-alanine) was inserted between the fluorophor and the peptide. sPIF-1$_{15}$ (SEQ ID NO: 13) was also labeled by adding Lysine at the C terminal. In addition, SMRT (SQAVQEHASTNMG) sPIF-2$_{13}$ (SEQ ID NO: 14), FITC and Biotin labeled were generated on the N terminal. Scrambled SMRT, scrPIF-2$_{14}$ (SEQ ID NO: 9), GQAS-SAQMNSTGVH; scrPIF-2$_3$ (SEQ ID NO: 8), EVAQH-SQASTMNG; and SGIVIYQYMDDRYVGSDL peptide (reverse transcriptase homologue-RTH) sPIF-3$_{18}$ (SEQ ID NO: 15) were also generated synthetically.

While the present invention is described with reference to PIF's derived from mammals like mice or humans, it is to be understood that the invention is not limited to these peptides. For example, PIF peptides or their antagonists which are cloned, synthesized, or isolated from mammals like horses, cows, or swine or substituted variants of these peptides may be used in the practice of various embodiments of the present invention. It is also contemplated that substitutions of amino acids in the peptide sequence of these PIFs can be made and used as would be known to those skilled in the art in the practice of various embodiments of the present invention. Such PIF variants may be characterized by their ability to alter the $T_H1/T_H2$ ratio of antigen stimulated cells or by their ability interact with PIF receptors on cells.

PIF-1 Peptides Enhance Rosettes Formation

FIG. 1 shows that sPIF-1$_{15}$ (SEQ ID NO: 13), binds to PBMC, which forms rosettes in their P-L assay. FIG. 1(A) depicts fluorescence-labeled sPIF-1$_{15}$ (SEQ ID NO: 13) binding to human lymphocytes in a dose dependent manner. FIG. 1(B) shows binding of FITC nPIF-1$_{15}$ (SEQ ID NO: 1) to the total PBMC population and FIG. 1(C) shows binding to lymphocytes that form rosettes with platelets, P-L bioassay, documents presence of nPIF-1$_{15}$ (SEQ ID NO: 1), receptors on the PBMC surface.

Human PBMC were isolated by the Ficoll method. FITC-labeled nPIF-1$_{15}$ (SEQ ID NO: 1) and (FITC)-labeled scrPIF-1 (SEQ ID NO: 5) and match-size irrelevant peptide (FITC)-labeled negative controls negPIF-1$_{15}$ (SEQ ID NO: 11), were dissolved in PBS at concentrations ranging from 0.75 to 48.19 µM, and were incubated with 500,000 lymphocytes for 1 h at room temperature. The cells were washed 6 times with PBS and resuspended in 500 µl of the same buffer. T-cells and monocytes identification was performed in independent experiments by incubation with anti-CD3 and anti-CD14 antibody-phycoerithryn (PE) labeled. nPIF-1$_{15}$ (SEQ ID NO: 1) binding to PBMC was determined by flow cytometry. In addition, rosettes formed by T cell-platelets were detected by flow cytometry using anti-CD3 antibody-PE and anti-CD41a antibody-FITC (all antibodies were from Pharmingen Inc.). These rosettes were not labeled by the control peptides (FITC)-labeled scrPIF-1$_{15}$ (SEQ ID NO: 5) and match-size irrelevant peptide (FITC)-labeled negative controls negPIF-1$_{15}$ (SEQ ID NO: 11). This indicates that both embryo culture media and serum contain similar peptides and provides evidence for the utility of biologic effects of the peptides and for the diagnostic potential using antibodies against the same.

The biological characteristics of preimplantation factors in vitro were determined employing the synthetic versions of both 15-residue sPIF-1$_{15}$ (SEQ ID NO: 13) and 9-residue sPIF-1$_9$ (SEQ ID NO: 16) isoforms, which exhibit similar biological activities in vitro. Flow cytometric determination of lymphocyte/platelet rosette formation shows that both sPIF-1$_{15}$ (SEQ ID NO: 13) and sPIF-1$_9$ (SEQ ID NO: 16) isoforms induce a four-fold increase in the number of rosettes in the presence of the anti-CD2 antibody (data not shown), demonstrating that they exhibit the same anti-CD2-blocking effect manifested by the embryo-conditioned culture medium and maternal serum.

In a further example, PIFs effect on PIF bioassay and flow cytometry was observed. Compared to control, the addition of PIF increased platelet/lymphocyte rosette formation as follows:

TABLE 2

| PIF | Increase in Rosette Formation |
| --- | --- |
| 1 nM | >370% |
| 10 nM | >288% |
| 100 nM | >208% |

Results indicate that synthetic PIF replicates the effects seen by pregnant serum and embryo culture media results.

PIF-1 Immune Effects

Human PBMC were isolated and cultured for 2-4 days in AIM-V medium containing 0 to 200 nM of sPIF-1$_{15}$ (SEQ ID NO: 13) or scrPIF-1$_{15}$ (SEQ ID NO: 5). The following proliferation-activating agents were used: anti-CD3 antibody (10 μg/ml solution) bound on the plate wells in the presence or absence of IL-2 at 10 μg/ml; phytohemmaglutinin (PHA) at 4 μg/ml. The effects of sPIF-1$_{15}$ (SEQ ID NO: 13) or scrPIF-1$_{15}$ (SEQ ID NO: 5) peptides were also determined by the mixed lymphocyte reaction (MLR) after 3 days in heterologous cultures of PBMC with cells previously treated with mitomycin C (100 μg/ml for 4 h). Cell proliferation was determined by tritiated thymidine incorporation (16 h) of 72-h culture. Cytokine release (IL-4, IL-10, IFN-γ and TNF-α) into culture supernatants was determined at 72 h of culture by ELISA (R&D System).

Figures 2A, 2B:
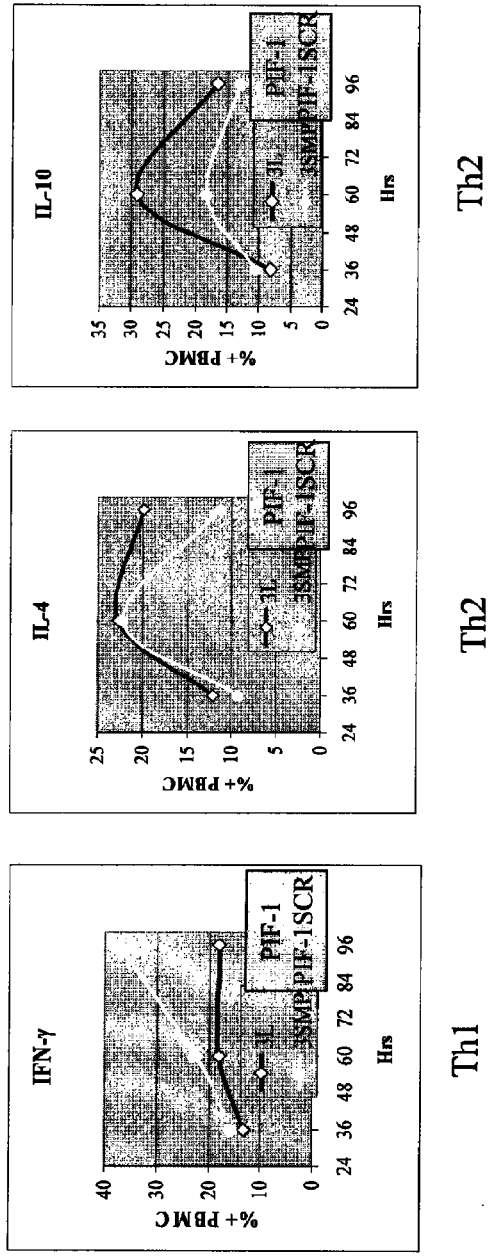

Overall, sPIF-1$_{15}$ (SEQ ID NO: 13) decreases the proliferation rate of human lymphocytes stimulated with diverse reagents and provokes a shift toward a T$_H$2 cytokine phenotype. sPIF-1$_{15}$ (SEQ ID NO: 13) negatively affects the proliferation of activated lymphocytes. Lower rates of lymphocyte proliferation was found at 250, 62.5 and 1 nM of sPIF-1$_{15}$ (SEQ ID NO: 13) for PHA, anti-CD3 antibody and MLR, respectively. The results were compared with CD3 antibody stimulated lymphocytes without sPIF-1$_{15}$ (SEQ ID NO: 13) or with scrPIF-1$_{15}$ (SEQ ID NO: 5) used as controls. IL-10 release is significantly increased in the culture supernatants and IFN-γ release is significantly decreased by exposure to sPIF-1$_{15}$ (SEQ ID NO: 13). In contrast, sPIF-1$_{15}$ (SEQ ID NO: 13) does not have a significant effect on IL-4 or TNF-α release As show in FIG. 2B, sPIF-1$_{15}$ (SEQ ID NO: 13) increases the T$_H$2/T$_H$1 cytokine ratio in PBMC more than five-fold, owing mainly to the substantial increase of IL-10 coupled with a decrease in IFN-γ. Number of IL-10 secreting cells also increased (50-60%) starting at day 2 and peaking at days 3-4 and preceding the IFN-γ decreases (30%) by one day, suggesting that a causal relationship is likely in place with respect to the dynamics of these cytokines, as show in FIG. 2A. In contrast, same concentrations of scrPIF-1$_{15}$ (SEQ ID NO: 5) had no effect, as demonstrated by intracellular staining and flow cytometry.

These results demonstrate that sPIF-1$_{15}$ (SEQ ID NO: 13) has immunomodulatory effects that may lead to the development of an immune environment that is favorable to or at least tolerant for the presence of the early embryo. The T$_H$2/T$_H$1 cytokine ratio was determined at different concentrations of sPIF-1$_{15}$ (SEQ ID NO: 13). Similar dose dependent results at the 1-500 nM range were found in PHA and MLR activated lymphocytes by effects of sPIF-1$_{15}$ (SEQ ID NO: 13) and sPIF-1$_{(9)}$ (SEQ ID NO: 16). Similar results were obtained with sPIF-2 (SEQ ID NO: 14), compared to scrPIF-2$_{13}$ (SEQ ID NO: 8).

PIF Correlates with an In-Vivo Pro-Inflammatory Response

PIF activity was measured in normal (n=4) and thrombophilic pregnancies (n=4) using a FC bioassay based upon CD2 binding to Jurkat leukemia cell line. A correlation between PIF activity and IL-1 in normal pregnancies was observed, but not in thrombophilic conditions (p=0.02). No correlation was observed between PIF and TNF α, IL-8 or thrombus precursor protein (TpP) in either normal pregnancies or thrombophilic conditions. Results appear to indicate that the embryo directs maternal immune response, rather than playing a passive role and that PIF may be an early indicator of pregnancy well-being.

Dynamics of Synthetic PIF-1 Interaction with Resting/Activated PBMC

Figure 3:
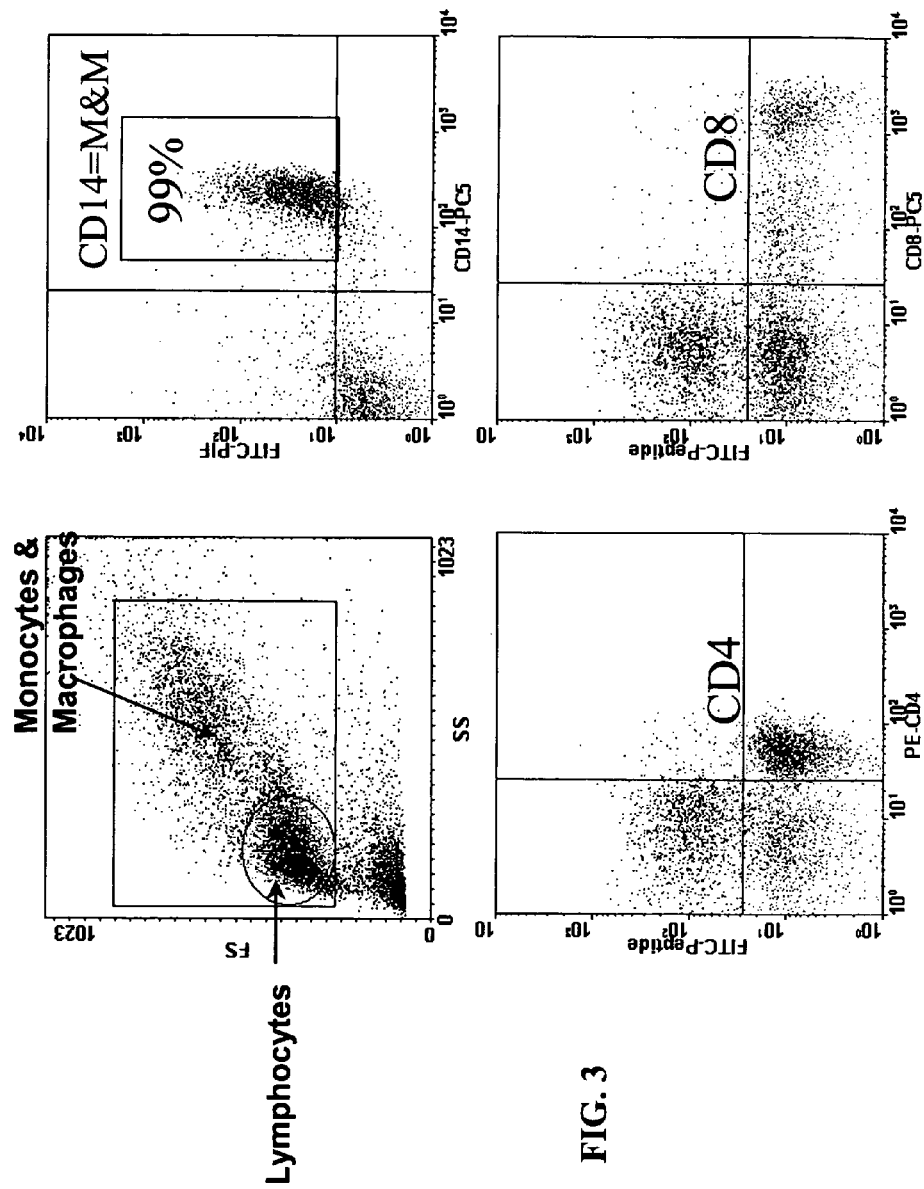
FIG. 3. shows preferential binding of FITC sPIF-1 (SEQ ID NO: 13) to subpopulation of PBMC. sPIF-1 binds monocytes and macrophages (primary antigen presenting cells) at the basal state. FITC labeled PIF-1 was added to unstimulated PBMC. Binding of the labeled peptide to PBMC subpopulation was determined by using specific CD markers. CD14+ cells represent monocytes.

The expression of PIF binding sites was examined utilizing flow cytometry studies employing FITC labeled sPIF-1$_{15}$ (SEQ ID NO: 13) and PBMC from normal human donors showed that it binds to a small number of naive T cells. As shown in FIG. 3, sPIF-1$_{15}$ (SEQ ID NO: 13) binds to monocytes and macrophages, the primary antigen presenting cells, at basal state. In contrast, PHA-stimulated sPIF-1$_{15}$ (SEQ ID NO: 13) binds all monocytes but not to platelets. Without wishing to be bound by theory, this suggests that monocytes and a sub-set of T cells express prior to pregnancy receptors, and also indicates that although sPIF-1$_{15}$ (SEQ ID NO: 13) is somehow similar enough to CD2 that it binds to anti-CD2, it does not bind to the platelet marker CD58, as does CD2 itself. PIF-1 sequence has no homology to that of CD2.

Figure 4:
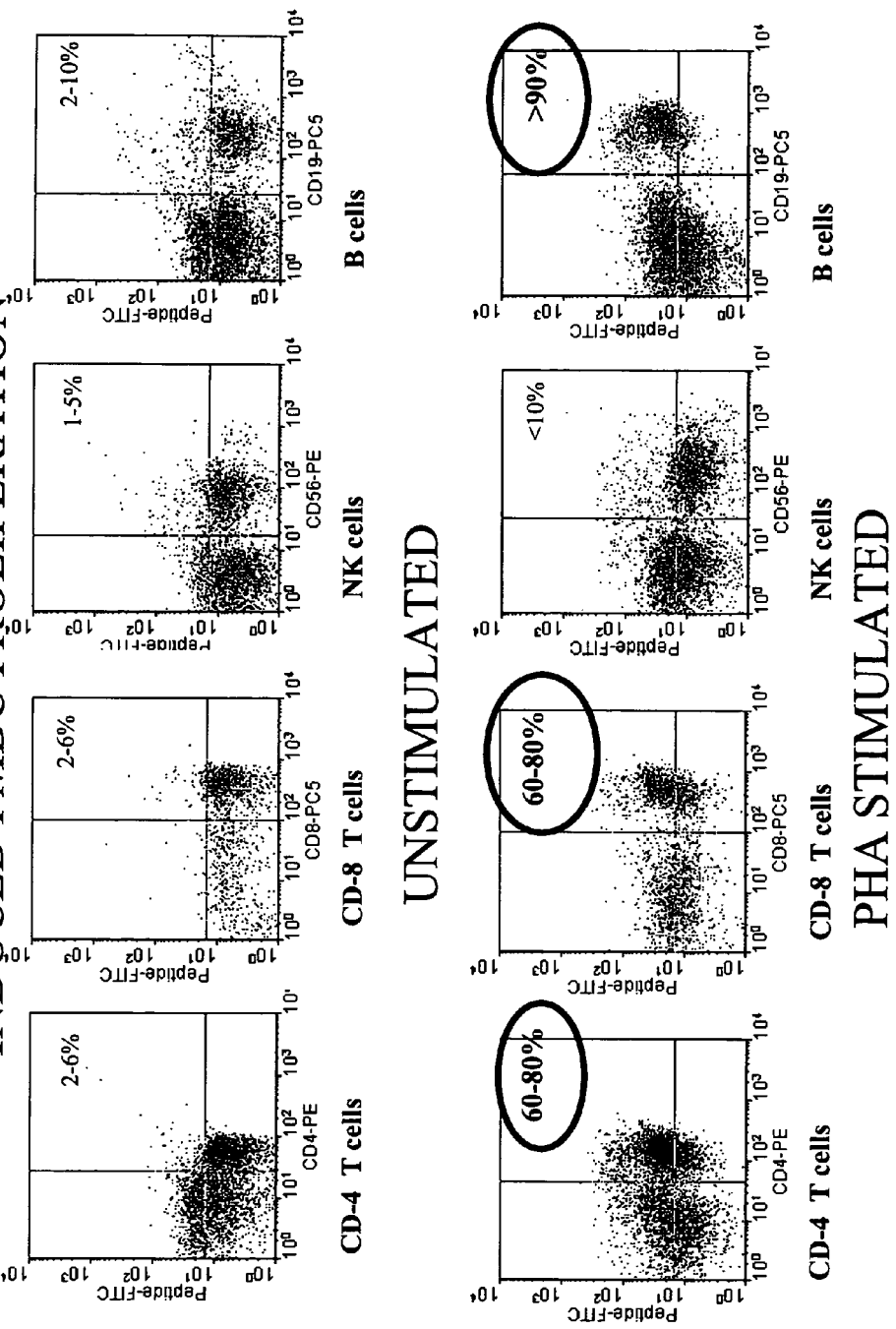
FIG. 4 shows effects of binding by FITC $sPIF-1_{15}$ (SEQ ID NO: 13) to basal and PHA stimulated PBMC PIF receptors. Expression of $PIF-1_{15}$ (SEQ ID NO: 1), receptor following PHA induced PBMC proliferation CD-4 T cells; CD-8 T cells; NK cell and B cells (unstimulated-top); (PHA stimulated-bottom). Flow cytometry analysis of PBMC following exposure to FITC $sPIF-1_{15}$ (SEQ ID NO: 13), % expression was determined in PBMC subtypes before and after exposure to 1 ug/ml PHA for 24 hours. There was a major increase in PIF-1 (SEQ ID NO: 1) receptors expression on T (CD4, CD8 cells, 60-80%) and B cells (>90%) while no changes in the NK cells receptors was noted. This indicates that both T cells (cellular immunity) and B cells (antigen presenting cells) increase PIF-1 receptor expression markedly within 24 hours. While macrophages/monocytes have already a full complement of PIF receptors (first responders). In contrast, minimal receptors expression could be induced by the mitogen on NK (natural killer) cells that are supposed to be protect the body's basal immune response. The delay seen by PIF effects on mitogen induced PBMC cytokines secretion (24 h following exposure) may be explained by requirement for receptor induction (takes 24 hours). Therefore an only 4 hours exposure had no effect (see Table 1).
Figure 5B:
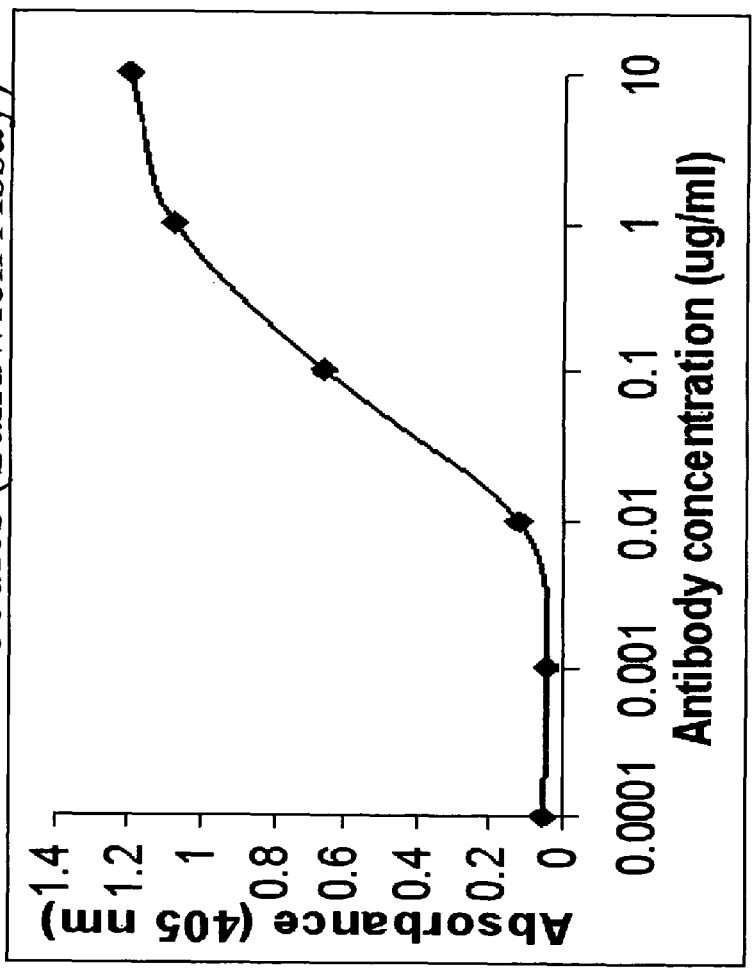
FIG. 5B shows ELISA profile of high affinity PIF-1 IgY antibodies (sandwich assay). Chicken were injected with KLH bound PIF-1 and the eggs were collected and affinity purified on a PIF column.

Using flow cytometry fluoroscein-labeled sPIF-1$_{15}$ (SEQ ID NO: 13) binding to immune cells was examined on resting PBMC. Monocytes (CD14+ cells) express binding sites on most cells, while the expression on resting T cells (CD4+ and CD8+), B cells (CD19+) or NK cells (CD56) populations remained very low. As shown in FIG. 4, within 24 hrs of activation by PBMC cultured with the T-cell mitogen, phytohemmaglutinin (PHA)), 60-80% of T lymphocytes (T helper cells, T cytotoxic cells), and >90% of B cells became positive for the fluorescent sPIF-1$_{15}$ (SEQ ID NO: 13) binding, demonstrating that lymphocytes can recognize preimplantation factors and may respond to them but only if activated. NK cells did not appear to bind sPIF-1$_{15}$ (SEQ ID NO: 13) even after several days in culture with PHA.

Scrambled PIF-1 Synthetic Peptide Acts as Antagonist to PIF-1 scrPIF-1$_{15}$ (SEQ ID NO: 5) has an identical amino acids composition as sPIF-1$_{15}$ (SEQ ID NO: 13) but the sequence is in random order. When used as a control for sPIF-1$_{15}$ (SEQ ID NO: 13) the FITC scrambled peptide scrPIF-1$_{15}$ (SEQ ID NO: 5) did bind to PBMC as determined by flow cytometry. Increasing concentrations of scrPIF-1$_{15}$ (SEQ ID NO: 5) reduced the binding of fluorescent sPIF-1$_{15}$ (SEQ ID NO: 13) peptide suggesting that scrPIF-1$_{15}$ (SEQ ID NO: 5) acts on the same receptor as sPIF-1$_{15}$ (SEQ ID NO: 13). This was further confirmed by the antagonistic effect noted by scrPIF-1$_{15}$ (SEQ ID NO: 5) effect on PBMC proliferation. PHA or anti-CD3 antibody induced proliferation was dramatically blocked by low concentrations of scrPIF-1$_{15}$ (SEQ ID NO: 5) (125-1000 nM). Addition of the antagonist scrPIF-1$_{15}$ (SEQ ID NO: 5) (125 nM) blocked also sPIF-1$_{15}$ (SEQ ID NO: 1) effect on IL10 secretion. scrPIF-1$_{15}$ (SEQ ID NO: 5) also blocked the effect of sPIF-1$_{15}$ (SEQ ID NO: 13) induced increase in beta integrin expression by human endometrial cells.

scrPIF-1$_{15}$ (SEQ ID NO: 5) reverses sPIF-1$_{15}$ (SEQ ID NO: 14) induced inhibition of PHA triggered PBMC proliferation. Isolated PBMC were stimulated by PHA (4 ug/ml) and cultured 2-4 days with sPIF-1$_9$ (SEQ ID NO: 16) (0-125 nM)+/−scrPIF-1$_{15}$ (SEQ ID NO: 5) 125/nM. PBMC proliferation was determined by 3H Thymidine incorporation. *=p<0.05.

scrPIF-1$_{15}$ (SEQ ID NO: 5) also reverses sPIF-1$_{(9)}$ (SEQ ID NO: 19) induced inhibition of mAbCD3 triggered PBMC proliferation. Isolated PBMC were stimulated by plate bound antiCD3 antibody (10 ug/ml) and cultured 2-4 days with sPIF-1$_9$ (SEQ ID NO: 16) (0-125 nM)+/−scrPIF-1$_{15}$ (SEQ ID NO: 5) 125/nM. PBMC proliferation was determined by 3H Thymidine incorporation. *=p<0.05.

scrPIF-1$_{15}$ (SEQ ID NO: 5) also reverses sPIF-1$_{(9)}$ (SEQ ID NO: 16) induced IL10 secretion by PBMC following PHA exposure. Isolated PBMC were stimulated by PHA (4 ug/ml) and cultured 2-4 days with sPIF-1$_{(9)}$ (SEQ ID NO: 16) (0-15 nM)+/−scrPIF-1$_{15}$ (SEQ ID NO: 5) 125/nM. IL10 secretion was determined by ELISA *=p<0.05.

In scrPIF-1 inhibitory action appears to be exerted on the PIF binding site. Both PIF-1 and scrPIF-1 bind specifically to isolated mouse splenocytes receptors. Based on flow cytometry data it appears that the binding of both peptides was for the same site therefore explaining the clear antagonistic effect of scrPIF-1 on PIF-1 on both cytokine secretion and PBMC proliferation (see below).

Overall, the results from PIF effects on PBMC proliferation, cytokine release and cytokine content of PBMC indicate a major inhibitory effects on cell proliferation and modulation of cytokines secretion and their cellular content. This only noted only under mitogen activated conditions, while PIF alone had no effect. In addition, an increase in some $T_h1$ type of cytokines is also required to protect the maternal organism against infection. The examples of mitogens that were used are highly potent. In contrast, the embryo as it develops on a practical basis until hatching is surrounded by the protective zona pellucida. Therefore the immune reaction towards the embryo by the mother until implantation (where direct contact is established is minimal, and is gradual allowing for development of tolerance in gentle manner. In contrast PIF-1 scr has practically no effect except for stimulating TNFalpha, a $T_h1$ type cytokine.

PIF Likely Acts Through an Inducible Unique Immune Cell Surface Receptor

Fluorescent PIF peptides bind to immune cell membranes following activation. In order to better evaluate the receptor site that is an activation marker, flow cytometry (FC) using specific CD marker antibodies was performed. CD69 is expressed during activation of lymphocytes and monocytes, and is a marker of NK cells activation. CD25 is the receptor for IL-2, and a known activation marker as well. The size of these molecules' positive cell population did not correlate with the sPIF-1$_{15}$ (SEQ ID NO: 13) positive populations. This confirmed that PIF receptors in the immune system are unique and selectively expressed on subpopulation of immune cells and they are inducible by mitogenic activation. scrPIF-1$_{15}$ (SEQ ID NO: 5) inhibitory action appears to be exerted on the PIF binding site.

PIF-1 Enhances Endometrial Receptivity

Human endometrial tissues were digested and stromal and epithelial cells (hEEC) isolated and cultured with a fetal bovine serum (FBS)-enriched medium until confluent layers were obtained. After that the cells were cultured for two more days in a FBS free—medium followed by a further 2-day culture in the same medium containing PIF peptides (1-500 nM). The expression of β-3 integrin by hEEC was qualitatively determined by immunocytochemistry and quantitatively measured by flow cytometry using a specific anti-β-3 integrin monoclonal antibody (SS A6). sPIF-1$_{15}$ (SEQ ID NO: 13) and 9-residue sPIF-1$_9$ (SEQ ID NO: 16) isoforms and sPIF-2$_{13}$ (SEQ ID NO: 14) treatment of hEEC exhibits up to a four-fold increase in the expression of β-3-epithelial integrin. These data indicate that preimplantion factor peptides released by the preimplantation embryo up-regulate the expression of an important marker for endometrial receptivity facilitating pregnancy initiation and maintenance.

In addition, to compare the recovery of β-3 integrin expression with PIF effects described after cultured hEEC in a free-fetal bovine serum (FBS) medium some cells were cultured again in FBS-medium. Interestingly, these cells expressed higher levels of β-3-integrin than did cells growing in free FBS-medium but still levels of β-3-integrin expression triggered by PIF effects were higher. In contrast, PIF did not interact with cultures of human endometrial stromal cells. These results could imply that PIF effects on β-3-integrin expression, which indicate an increase of endometrial receptivity, are higher that those triggered by a medium containing progesterone and an undefined variety and concentration of growth factors and hormones. Data using FITC PIF-1 showed that PIF binds to specific sites on epithelial cells.

PIF Identifies Abnormal Immune Response of a Patient with Recurrent Pregnancy Loss sPIF-1$_{15}$ (SEQ ID NO: 13) effect was tested on a patient with over 14 miscarriages and no live birth. Her immune cells were examined in the non-pregnant state, by exposure to sPIF-1$_{15}$ (SEQ ID NO: 13) using PBMC preparations. Induction of PIF receptor expression, and binding to lymphocytes were used to characterize the treated cells. Table 3 illustrates the ability of PIF assay to predict premature labor.

TABLE 3

| Specimen | PHA | (PIF+/CD4+)/ CD4+ | (PIF+/CD8+)/ CD8+ | (PIF+/CD19+)/ CD19+ |
|---|---|---|---|---|
| Control | + | 22.1 (0%) | 24.5 | 46.2 |
| Patient | + | 16.2 (−27%) | 16.3 (−33%) | 48.2 |

The patient's PIF receptors appear to be inducible by PHA as are those of the control subject. No differences were observed on B cells, but patient's T cells PIF receptor were ~30% less than the control. Table 4 shows ability of PIF assay to correlate with proinflammatory cytokines in coagulation disorder associated with pregnancy (thrombophylia).

TABLE 4

PIF-1 Effects on Cytokine Expression

| Specimen | PHA | PIF-$1_{15}$ | TNFα* | IL-10* | $T_H1/T_H2$ |
|---|---|---|---|---|---|
| patient | − | − | 7.98 | 7.77 | 1.03 |
| patient | + | − | 14.23 | 24.76 | 0.57 |
| patient | + | + | 18.32 | 24.32 | 0.75 (+32%) |
| control | − | − | 4.76 | 4.71 | 0.99 |
| control | + | − | 17.43 | 25.72 | 0.68 |
| control | + | + | 15.46 | 28.18 | 0.55 (−19%) |

*) All cytokine numbers are % of total PBMC in scatter gate (including CD14) and 4 in table above).

Under sPIF-$1_{15}$ SEQ ID NO: 13) influence, the $T_H1/T_H2$ ratio decreases (as expected) in the control specimen; but the same did not decrease in the patient's PBMC culture media (see bold numbers in table above).

The results obtained with this illustrative clinical case indicate that changes in the immune system of patients with poor obstetric history can be identified prior pregnancy by using PIFs as an embryo surrogate. Such testing can allow for pre-pregnancy identification of patients with poor ability to mount an immune change or tolerance to initiate and maintain pregnancy. Such an insight could help in screening patients at risk of miscarriage and lead to correction of the underlying pathologic condition perhaps by PIF administration. Such testing can be applied during pregnancy as well. Moreover, adding PIF to test the patient's endometrial cells properties (beta integrin or such), following collection by biopsy may help to determine whether the mother is able to respond to the presence of the embryo by increased receptivity.

Generate Polyclonal Antibodies to the Synthetic PIF-1, PIF-2 and PIF-3 Peptides To generate specific antibodies against sPIF-$1_{15}$ (SEQ ID NO: 13) conjugation to carrier, Keyhole Limpet hemocyanin (KLH) was carried out. sPIF-$1_{15}$ (SEQ ID NO: 13) was conjugated to KLH either on the carboxy or amine terminus of the molecule to cover potential differences in immunogenicity related to peptide presentation. The two peptide-carrier conjugates generated were injected into two rabbits. Within a 5-week immunization protocol all 4 rabbits responded by generating a high titer serum, with a titer of 1:50,000-1:150,000. The titer strength appeared to increase with the second bleeding. These rabbits may serve as a long-term reservoir of serum for antibody generation AbPIF-$1_{15}$. The rabbits may continue to be injected with immunogens on a monthly basis, collecting sera periodically and testing for titer and affinity. Antibodies to other PIFs, including AbPIF-$2_{13}$ and AbPIF-$3_{18}$, were generated with the same method using KLH bound peptide in the amine terminal. Rabbits bled 8 weeks after immunization yielded 1:25,000 titers for both peptides with detection of the PIF peptides to the nanomolar region. These antibodies were affinity purified using PIF-1, PIF-2 and PIF-3 bound affinity columns. The purified antibodies were conjugated each to a separate affinity column and they will serve for isolation of PIF peptides from various biological fluids.

Monoclonal antibodies to PIF-1 were developed as well. A hybridoma cell that produces a monoclonal antibody specific for a PIF polypeptide, and culturing the cell under conditions that permit production of the monoclonal antibody.

Such PIF antibodies may be used in assay as well as in therapeutic treatment (vaccination) of patients. For example, PIF peptide conjugates may be used as antigen (vaccine) to fight malaria. PIF itself, being a minimal unit might behave as a better antigen than the when its sequence is embedded in the intact, full length circumsporozoite protein in the malaria outer cell membrane. In another example, PIF antagonist (a peptide or other chemical shown to bind to PIF receptors, and block PIF function) or any procedure whereby such compound is used as drug, may be useful to treat malaria or block malaria propagation in the human body (by blocking the sites through/by which the parasite controls and paralyses the immune system and allows it to proliferate). Similarly, any humanized or horse antibodies to PIF or a procedure whereby these are used as agents may be used for passive immunization for malaria. (assuming such antibodies must recognize the circumsporozoite protein on the malaria parasite).

In one example, polyclonal antibodies AbPIF-$1_{15}$ were generated against sPIF-$1_{15}$ (SEQ ID NO: 13) in rabbits (Covance Inc.). High titers 50% at 1:50,000 were achieved. Serial dilutions of synthetic sPIF-$1_{15}$ (SEQ ID NO: 13) were plated, blocked and then washed off. PIF-1 antibody (1:5000) was added incubated and washed off. Goat anti-rabbit antibody was added, incubated and washed off. Reaction was stopped by SDS and counted in plate reader (Biosynthesis Inc, G Vandydriff). As shown in the ELISA standard curve of FIG. 4, PIF antibody detects low sPIF levels (pg). The antibody affinity was also confirmed by using a competition analysis between biotin labeled and unlabeled nPIF-$1_{15}$ (SEQ ID NO: 1) (data not shown). Also when scrPIF-1 (SEQ ID NO: 5) was tested in the assay the antibody did not recognize it attesting to the high specificity of the antibody that was generated.

FIG. 3A demonstrates the affinity of PIF-1 IgY antibodies. Peptide as test antigen. Affi-pure IgY as the primary antibody and goat anti-Ig-Y as the secondary antibody. A fixed amount of antigen (5 ug/ml) and serial dilution of IgY.

FIG. 3B demonstrates the specificity of PIF-1 polyclonal antibody. At 4.5 ug/ml pAb coating concentration, PIF-$1_{15}$ was detectable at 10-30 pM in a dose response curve with an $IC_{50}$ of 500-700 pm, and linearly up to 30 nM. scrPIF-1 did not compete with biotinylated peptide, as the native. No binding appears to occur on uncoated plates, yielding a good background. Results demonstrate that PIF-1 polyclonal antibody appears to avoid false positives and negatives.

In one non-limiting embodiment, a PIF-based pregnancy diagnosis utlilizing an ELISA or yes/no stick in the form of a kit is provided. The components of the PIF ELISA kit may include, for example, HRP-Avidin, PIF-Biotin and anti-PIF-$1_{15}$ antibody. In the absence of PIF in the test sample, HRP enzyme would bind to the antibody through the PIF-biotin complex, generating a maximum color. In the presence of PIF in the test sample, PIF binds to the PIF antibody and prevents the HRP enzyme complex from binding, generating a minimum color.

Figure 6:
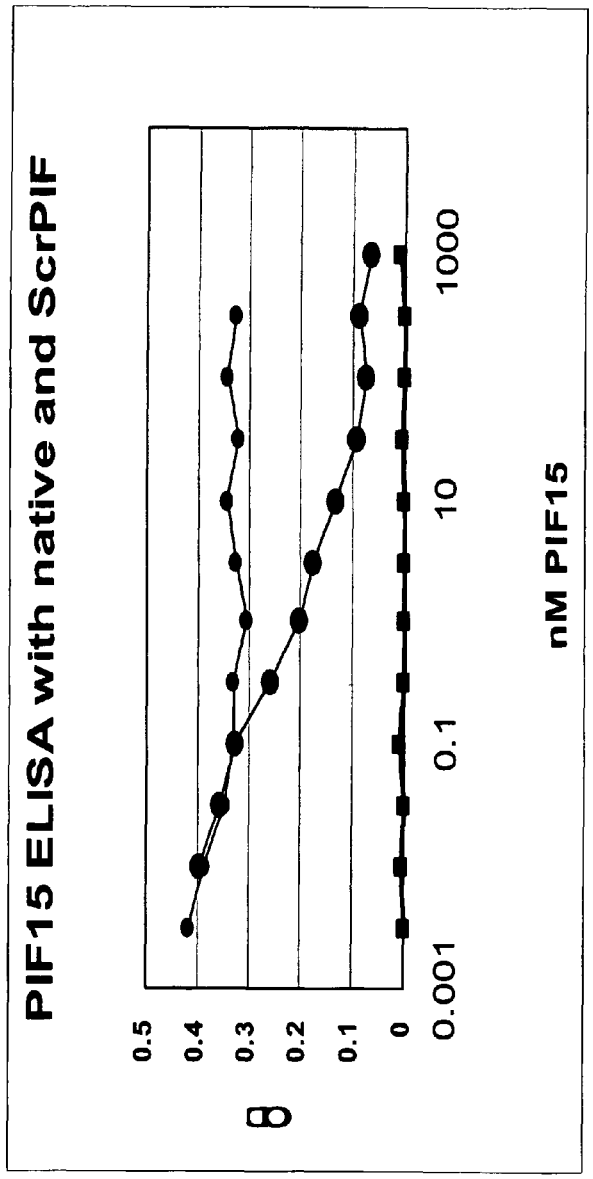
FIG. 6 shows ELISA profile of $nPIF-1_{15}$ and $scrPIF-1_{15}$ using Biotin labeled versus unlabeled peptide where the antibody captures the peptide in the unknown samples and compares it to standards (see FIG. 7).
Figure 7:
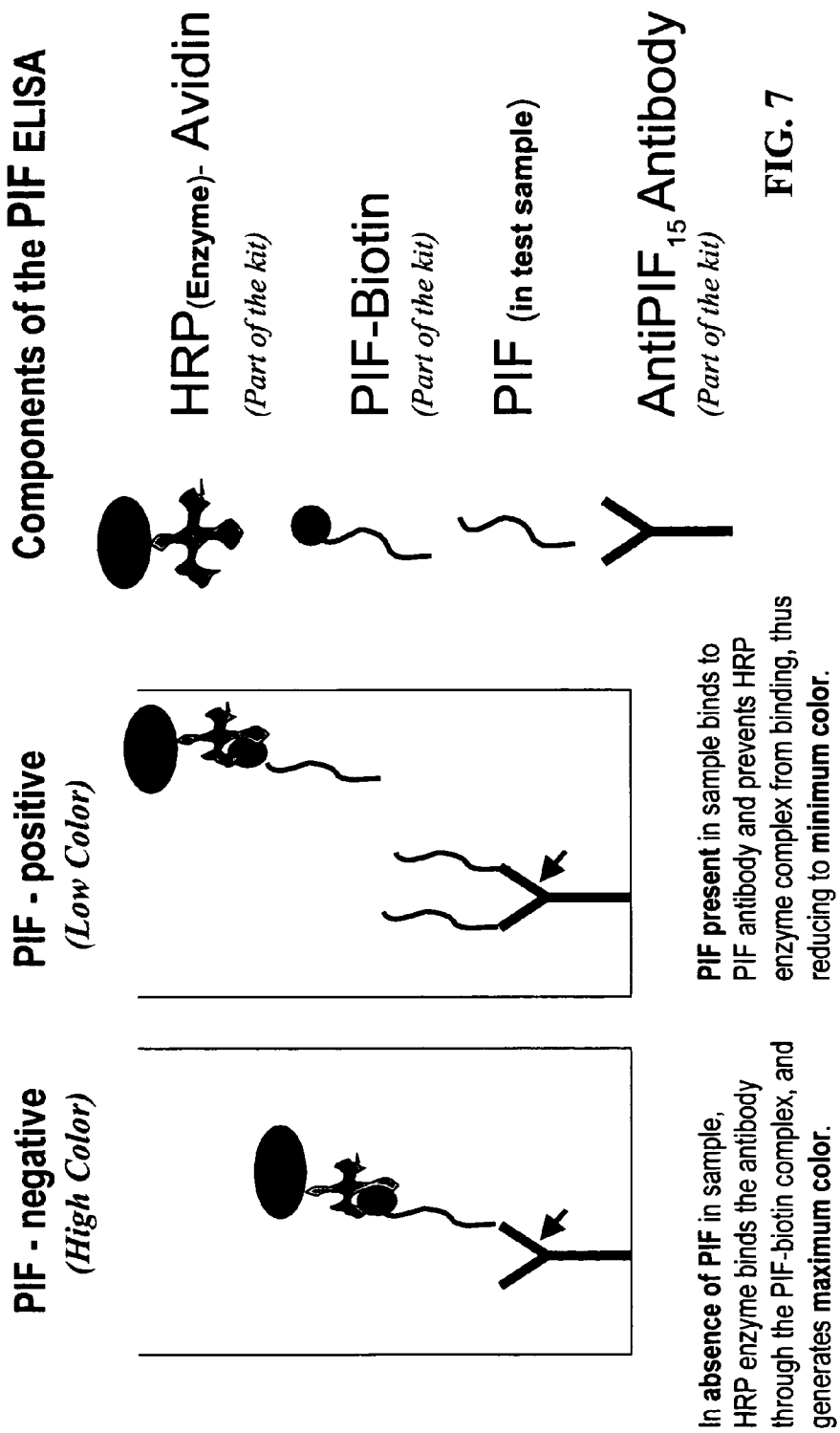
FIG. 7 depicts an example of a PIF-based diagnostic of the present invention. Four clones of monoclonal antibodies to $PIF-1_{15}$ were developed as well in mice and ascites fluid was generated with high affinity antibodies as hybridomas with sustained MAb production.

Isolation and Identification of PIF Like Proteins in Human Placenta and Other Fetal Tissues Using affinity purified PIF IgG 1, 2 and 3 and Igy PIF-1, PIFs were identified in human term placenta using Western blot. Human placenta was the test antigen. Lanes 1 and 3 were loaded with 50 ug of antigen per lane and lanes 2, 4 and 5 were loaded with 100 ug of antigen per lane. Lanes 1 and 2 were incubeted with affi-pure anti-PIF-1 igY in a 1:50 dilution, goat anti-IgY-HRP in a 1:1000 dilution. Lane 3 was incubated with anti-PIF-1 antibody in 1:200 dilution. Lane 4 was incubated with anti-PIF-2 antibody in 1:50 dilution. Lane 5 was incubated with anti-PIF-3 antibody in 1:50 dilution and goat/anti-rabbit-HRP in a dilution of 1:1000. Results of western blot are shown in FIG. 6.

Expression of PIF-1 in human pregnancy tissues was examined using affinity purified IgG using immunohistochemistry methods. Intense trophoblastic expression was found in first and second trimester placenta while expression was low at term. With respect to the 14-18 weeks fetus using a tissue array (60 samples, covering practically all organs). The highest expression was in the spleen and liver, with lesser in the adrenal, stomach and small bowel with no detectable expression in the esophagus and several other organs. The presence of PIF was also measured in the adrenal tissue, stomach, small bowel, thyroid and other organs (not shown). Non relevant IgG was used as controls.

Overall this indicates that PIF-1 is expressed in the human placenta and fetus across gestation where it declines at term to facilitate the process of delivery by lowering maternal tolerance for the fetus. With respect to the fetus highest expression are found in hemopoietic organs where immune reaction is expected to be the highest.

In another example, PIF-1 associated proteins were identified in human placental tissue. Term human placental homogenates were passed through an affinity column of PIF-1 antibody. The mass spectrometry profile following elution by PIF-1 antibody affinity column. Various PIF-1 associated proteins were identified and sequenced following affinity chromatography, including (NM_000039) apolipoprotein A-I precursor [Homo sapiens], electron-transferring-flavoprotein dehydrogenase, (BC017165) similar to triosephosphate isomerase 1 [Homo sapiens], (NM_052925) leukocyte receptor cluster (LRC) member [Homo sapiens], (NM_018141) mitochondrial ribosomal protein S10; mitochondrial 28S ribosomal protein S10 [Homo sapiens], (NM_000518) beta globin [Homo sapiens], (BC012292) heat shock 27 kDa protein 1, stress responsive, estrogen regulated [Homo sapiens] P04792.40, Estradiol beta 1 dehydrogenase 1 P14061.13, Fetal Beta MHC binding factor Q 14297.01, microtubule-associated protein 1A (proliferation-related protein p80 P78559.40). Some of those proteins were not previously described in the placenta. The proteins sequenced appear to show roles in immune function, cytoskeleton, enzyme function, and protein synthesis and cell proliferation. None of the sequenced proteins have sequence homology with PIF-1, therefore it likely reflects, in some cases, that PIF is attached to these proteins reflecting a protein-protein interaction related to the peptides function.

Demonstration that PIF is Present in the Placenta of Sheep

Placental tissues were collected from a mid-gestation sheep fetus. The placenta was embedded in paraffin and slides were prepared. Representative slides exposed to the 1/100 dilution of rabbit AbPIF-$1_{15}$ antibody. Compared with the non immunized serum, AbPIF-$1_{15}$ antibody intensely stained the placenta, as shown in FIG. 8. The DAKO Chemmate system on the autostainer with DAB as the substrate was used. Moreover, the binding was highly specific since no adjacent maternal tissues appeared to be stained by the antibody. As such, AbPIF-$1_{15}$ antibody as well as AbPIF-$2_{13}$ and AbPIF-$3_{18}$ could be useful in identifying presence of PIF in pregnant tissues. Gestational changes: Visual analysis was carried out on day 50 (n=4), day 80 (n=7), day 100 (n=7), day 128 (n=4) and day 135 (n=8) 9Term=145 days). Based on visual assessment of percent staining, placental levels were highest at day 50 and then declined to day 80 after which they remained constant. This pattern reflected the observations that were made with the human placenta.

In terms of localization, PIF-1 is localized to the ovine maternal-fetal interface which is comprised of fetal trophoblast and maternal epithelium. Interestingly, PIF-1 is localized to the binucleate trophoblast cells. These are non-proliferative migratory cells which fuse with the maternal epithelium to form a hybrid maternal-fetal syncytium. On many of the slides there appears to be epithelial staining. Some of this may come from the fetal contribution to this layer. Later in gestation, the staining becomes more restricted to the binucleate trophoblastic cell population.

PIF-1 expression decreases at term of growth restricted fetuses. A comparison of the placental growth restricted group (n=14) to the controls (n=14) at day 80 (placental growth period) gave no significant differences. In late gestation, there is evidence of a decrease in PIF1 in the growth restricted group compared with controls.

Isolation of PIF Peptides from Serum of Pregnant Mammals

Figure 11:
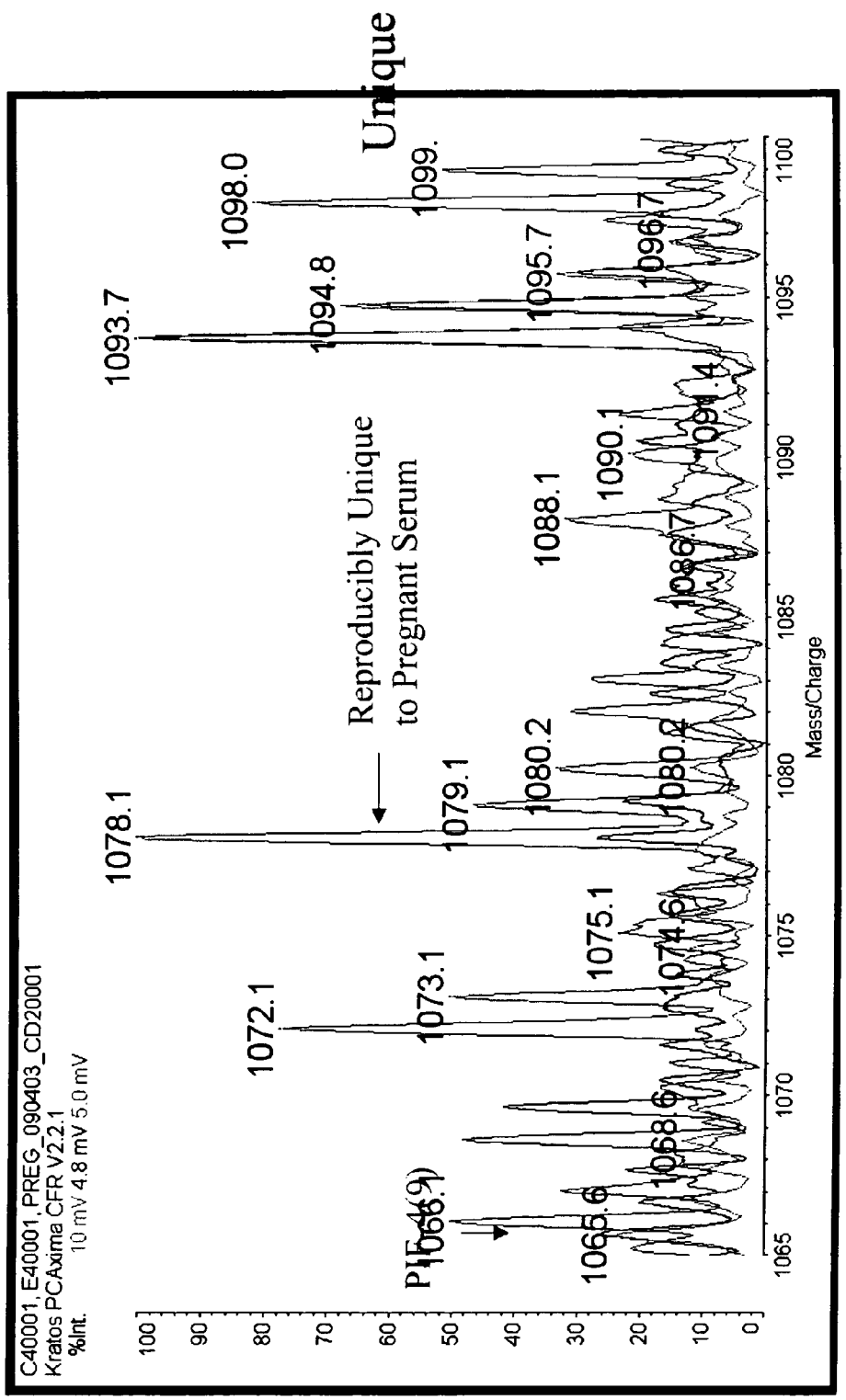
FIG. 11. Mass spectrum based identification of PIF peptides in pregnant pig serum as compared to non-pregnant serum following the use of CD2 based affinity column. Mass of the peptides in the non-pregnant v. pregnant samples revealed significant differences at the 900-1100 molecular weight region, where three distinct peptides were identified.
Figure 12:
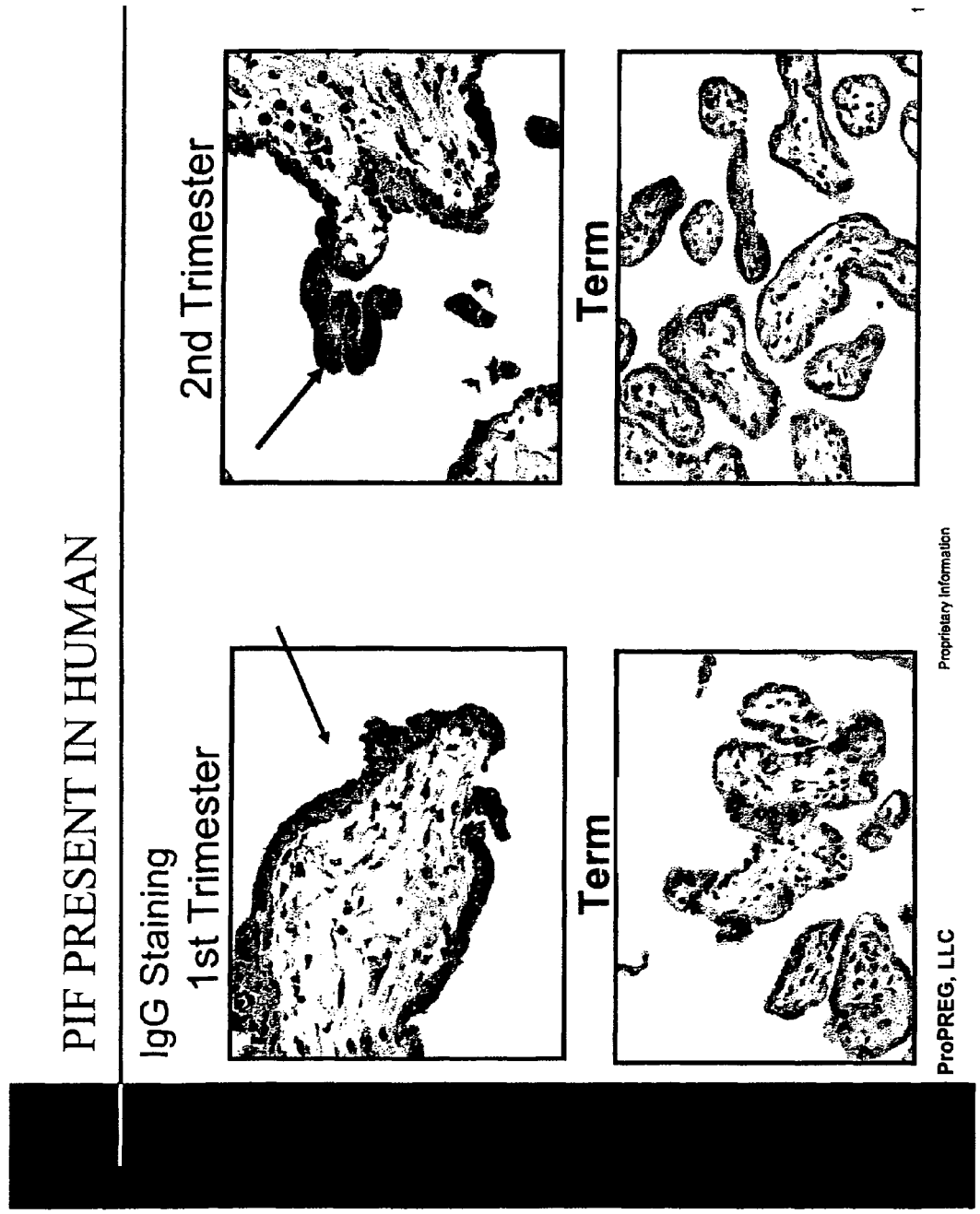
FIG. 12. PIF-1 IgG staining of human placenta during the first trimester, second trimester high in the trophoblastic layer while it declined at term.

Blood was collected from known pregnant sow. Serum was separated by centrifugation and the serum was stored at 20 C until use. The collected serum was filtered through a <3 kDa Amicon membrane. The filtrate was further subjected to a CD2 affinity column, as shown in FIG. 10. The collected samples were prepared and mass spectroscopy used to determine the molecular weight of samples by MALDI-TOF workstation. The molecular weight of samples was compared with non-pregnant porcine samples prepared in parallel. A number of peptides unique to pregnancy were isolated molecular weight range of about 1030-1100 daltons as shown in FIG. 11.

In another example, PIF-1 ELISA was used to detect pregnancy in pigs and cows. Using the PIF-1 ELISA competitive Biotin assay, known pregnant and non-pregnant samples were tested. Heat inactivated serum samples were diluted 1/30 and 1/100 and a low dilution difference between pregnant and non-pregnant samples were found for sows and a cow. The estimated PIF-1 in the pregnant sera are 10-30 nM. The heat inactivation helped to reduce the background of the assay generated by some high molecular weight proteins that were recognized by the PIF-1 antibody seen be Western blot (data not shown).

In a further example, serum samples were obtained at weekly intervals from twenty (20) women in a cross-sectional study (eight (8) in the first trimester, seven (7) in the second trimester, and five (5) in the third trimester) and two (2) women from 5-40 weeks gestation. All women had measurable PIF activity present in serum samples using bioassay. No PIF activity was detected in umbilical cord serum using bioassay. Results indicated that PIF is present throughout various stages of pregnancy.

Genome Analysis

Ten genes isolated from human placenta were analyzed. Seven of the 10 genes were annotated for both human (Hs) and mouse (Mm) genomes. When these were researched on the mouse microarray dataset for preimplantation development, using either Mm or Hs unigene identifiers returned the same result.

Although the present invention has been described in considerable detail with reference to certain preferred embodiments thereof, other versions are possible. For example any use of affinity column generated by using PIF-1, PIF-2 and PIF-3 antibodies for the isolation of PIF peptides from biological samples, any peptide derived from pre-implantation embryos that causes enhanced lymphocyte death by any mechanism (apoptosis, etc.), any modified PIF peptides that negate PIF activity and exert biological effects in order to increase immune reaction to enhance immune response in cancer, other immune suppressed conditions, like HIV; and any use of PIF-3 peptide to block HIV infection. A non limiting example is since PIF-3 and PIF-4 share homology with a region of HIV-1 RNA dependent DNA polymerase and the PIF-3 antibody recognizes such a domain on such a major region of HIV-1 virus such compounds could help negate or reduce infectivity of the virus by neutralizing and interdicting its penetration into the cell. The PIF-1 antagonist on the other hand could create a strong $T_H1$ type immunity thereby overcome immune suppressive conditions that are present for example in cancer. Therefore the spirit and scope of the appended claims should not be limited to the description and the preferred versions contain within this specification.

PIF-1 and Scr PIF-1 Contraceptive Effects in Mice

Preliminary in vivo assessment of PIF-1 antagonist by using PIF1scr/amide. With the view that PIF-1scr is a peptide, which, in general has a short half-life, estimated to be 30 minutes, a PIF-1scr was generated that had an additional amide group at the C terminus. This was an attempt to make the molecule more stable and have a longer half-life. Following the protocol below: (Dr Hoberman, Argus, Inc) PIF-1scr/amide was introduced two days after estrus to mice through an osmotic mini-pump (Alzet Model 2001; 1 ul/hr for 7 days) containing either 0.9% saline or 150 ug or 800 ug PIF-1scr/amide/day release in saline. The pumps were inserted subcutaneously under ketamine/xylazine anesthesia. Female mice were placed with male mice on the 3rd day afternoon of the expected estrus. Four different groups 5 each were studied, low and high dose PIF-1scr/amide, saline control, and one group with PIF-1. Mating was confirmed by the presence of sperm in the vagina or a copulatory plug the next morning. Pregnancy (or lack thereof) was determined by sacrificing on day 10 after breeding and the uterine horns were examined for implantation sites by using Chicago Blue solution. Results showed a trend towards lower number of implantation sites at the lower PIF-1scr/amide dose v. control group. This however did not reach statistical significance. No differences between high dose PIF-1scr/amide and controls were noted.

PIF-1 has no toxic effects following administration in early pregnancy to pregnant mice. This is evidenced by no significant effect on mouse fetuses number as well there was no effect on maternal body weights were noted among all the tested groups.

Scrambled PIF-1 by Intravaginal Administration May have a Non-Toxic Contraceptive Effect Female mice were mated with mice from the same strain. Subsequently, on day 0 (presumed day of mating) PIF-1 scr in saline solution was administered intravaginally twice daily for seven days (Dr Alan Hoberman, Argus, Inc). The dose was 800 ug/day, 150 ug/ml or saline vehicle only (5 animals in each group). Subsequently, mice were sacrificed at day 12 of presumed gestation and Caesarean-sectioned. Corpora lutea, implantation sites and live and dead embryos were recorded. A total of 2 animals in each of the treatment groups and one mouse in the control group failed to conceive. 4/10 of treated while 1/5 control animals conceived, the effect actually being all or none. No toxic or teratogenic effects were noted following the PIF administration since the number of implantation sites and viable embryos were unaffected in those mice that conceived Preliminary Study: PIF-1 Antibody and Scrambled PIF-1 Intravenous Administration is Non Toxic The contraceptive effect of either 150 ug of PIF-1scr in DMSO or 10 ug affinity purified PIF-1 (10 animals per group) or 20% DMSO solution (used as controls) was tested using single daily intravenous injections (Dr Alan Hoberman, Argus, Inc). Female mice were placed with male mice on the 3rd day afternoon of the expected estrus. Mating was confirmed by the presence of sperm in the vagina or a copulatory plug the next morning. Subsequently, were injected for 5 days one injection/day. Mice were sacrificed at day 12 of presumed gestation and Caesarean-sectioned. Corpora lutea, implantation sites and number of live and dead embryos were recorded. 2/10 mice in the PIF-1a and PIF-1 antibody group did not get pregnant, while in the control group all mice were pregnant. The effect was all or none since no toxic or teratogenic effects were noted in the mice that conceived.

Although the present invention has been described in considerable detail with reference to certain preferred embodiments thereof, other versions are possible. Therefore the spirit and scope of the appended claims should not be limited to the description and the preferred versions contain within this specification.

REFERENCES

1. S. R. Choudhury, L. A. Knapp, Hum. Reprod. Update 7, 113 (2001).
2. A. K. Abbas, K. M. Murphy, A. Sher, Nature 383, 787 (1996).
3. R. Raghupathy, Immunol. Today 18, 478 (1997).
4. T. G. Wegmann, H. Lin, L. Guilbert, T. R. Mosman, Immunol. Today 14, 353 (1993).
5. E. R. Barnea, K. I. Lahijani, R. Roussev, J. D. Barnea, C. B. Coulam, Am. J. Reprod. Immunol. 32, 133 (1994).
6. R. G. Roussev et al., Mol. Human. Reprod. 2, 883 (1996).
7. R. G. Roussev, E. R. Barnea, E. J. Thomason, C. B. Coulam, Am. J. Reprod. Immunol. 33, 68 (1995).
8. C. B Coulam, R. G. Roussev, E. J. Thomasson, E. R. Barnea, Am. J. Reprod. Immunol. 34, 88 (1995).
9. E. R Barnea et al., Am. J. Reprod. Immunol. 42, 95 (1999).
10. E. R. Barnea, C. B. Coulam, U.S. Pat. No. 5,981,198 (1999).
11. A. C. Cavanagh, H. Morton, Eur. J. Biochem. 222, 551 (1994).
12. E. Critser, J. English, in Immunological Obstetrics, C. B. Coulam, W. P. Faulk, J. A. McIntyre, Eds. (W. W. Norton, New York, 1992), pp. 202-215.
13. S. Heyner, Early Preg. 3, 153 (1997).
14. Circumsporozoite protein-malaria parasite (*Plasmodium falciparum*) (isolate NF54) (Protein accession number S05428).
15. G. Taubes, Science 290, 435 (2000).

16. SMARC32 a putative sperm transmembrane protein related to circumsporozoite protein (Protein accession number AAG31422).
17. D. L. Bodian, E. Y. Jones, K. Harlos, D. I. Stuart, S. J. Davis, Structure 2, 755 (1994).
18. M. P. Piccinni et al., Eur. J. Immunol., 8, 2431 (2001).
19. S. N. Wickramasinghe, S. H. Abdalla, Baillieres Best. Pract. Res. Clin. Haematol. 13, 277 (2000).
20. S. Romagnani, Annu. Rev. Immunol. 12, 227 (1994).
21. G. Chaouat et al., Immunol. 154, 4261 (1995).
22. H. Hong-Nerng et al., Fertil. Steril. 76, 797 (2001).
23. M. Y. Wu et al., Am. J. Reprod. Immunol. 46, 386 (2001).

What is claimed:

1. A method of enhancing implantation of one or more embryos in a subject comprising administering an effective amount of PIF peptide, wherein said PIF peptide is selected from the group consisting of SEQ ID NO:1, SEQ ID NO:2, SEQ ID NO:3, SEQ ID NO:4, SEQ ID NO:6, SEQ ID NO:7, SEQ ID NO:10, SEQ ID NO:12, SEQ ID NO:13, SEQ ID NO:14, SEQ ID NO:15, SEQ ID NO:16, SEQ ID NO:17 and combinations thereof.

2. The method of claim 1, wherein said administration is selected from in vivo and in vitro.

3. A method of decreasing the incidence of miscarriage in a subject comprising administering effect amount of PIF peptide to said subject, wherein said PIF peptide is selected from the group consisting of SEQ ID NO:1, SEQ ID NO:2, SEQ ID NO:3, SEQ ID NO:4, SEQ ID NO:6, SEQ ID NO:7, SEQ ID NO:10, SEQ ID NO:12, SEQ ID NO:13, SEQ ID NO:14, SEQ ID NO:15, SEQ ID NO:16, SEQ ID NO:17 and combinations thereof.

4. The method of claim 1, wherein said administration is to said subject.

5. The method of claim 1, wherein said administration is to said embryo.

6. The method of claim 1, wherein the amount of $T_H2$ cytokines in said subject is increased.

7. The method of claim 1, wherein the expression of beta-3-integrin in said subject is increased.

8. The method of claim 1, wherein said PIF peptide is selected from the group consisting of SEQ ID NO:1, SEQ ID NO:2, SEQ ID NO:3, SEQ ID NO:4 and combinations thereof.

9. The method of claim 3, wherein the amount of $T_H2$ cytokines in said subject is increased.

10. The method of claim 3, wherein the expression of beta-3-integrin in said subject is increased.

11. The method of claim 3, wherein said PIF peptide is selected from the group consisting of SEQ ID NO:1, SEQ ID NO:2, SEQ ID NO:3, SEQ ID NO:4 and combinations thereof.

12. A method of maintaining a pregnancy through term in a subject comprising administering an effective amount of PIF peptide to said subject, wherein said PIF peptide is selected from the group consisting of SEQ ID NO:1, SEQ ID NO:2, SEQ ID NO:3, SEQ ID NO:4, SEQ ID NO:6, SEQ ID NO:7, SEQ ID NO:10, SEQ ID NO:12, SEQ ID NO:13, SEQ ID NO:14, SEQ ID NO:15, SEQ ID NO:16, SEQ ID NO:17 and combinations thereof.

13. The method of claim 12, wherein the amount of $T_H2$ cytokines in said subject is increased.

14. The method of claim 12, wherein the expression of beta-3-integrin in said subject is increased.

15. The method of claim 12, wherein said PIF peptide is selected from the group consisting of SEQ ID NO:1, SEQ ID NO:2, SEQ ID NO:3, SEQ ID NO:4 and combinations thereof.

* * * * *

SEQUENCE LISTING

```
<160> NUMBER OF SEQ ID NOS: 17

<210> SEQ ID NO 1
<211> LENGTH: 15
<212> TYPE: PRT
<213> ORGANISM: Mus musculus

<400> SEQUENCE: 1

Met Val Arg Ile Lys Pro Gly Ser Ala Asn Lys Pro Ser Asp Asp
1               5                   10                  15

<210> SEQ ID NO 2
<211> LENGTH: 15
<212> TYPE: PRT
<213> ORGANISM: Mus musculus

<400> SEQUENCE: 2

Met Val Arg Ile Lys Tyr Gly Ser Tyr Asn Asn Lys Pro Ser Asp
1               5                   10                  15

<210> SEQ ID NO 3
<211> LENGTH: 13
<212> TYPE: PRT
<213> ORGANISM: Mus musculus

<400> SEQUENCE: 3

Met Val Arg Ile Lys Pro Gly Ser Ala Asn Lys Pro Ser
1               5                   10

<210> SEQ ID NO 4
<211> LENGTH: 9
<212> TYPE: PRT
<213> ORGANISM: Mus musculus

<400> SEQUENCE: 4

Met Val Arg Ile Lys Pro Gly Ser Ala
1               5

<210> SEQ ID NO 5
<211> LENGTH: 15
<212> TYPE: PRT
<213> ORGANISM: Artificial Sequence
<220> FEATURE:
<223> OTHER INFORMATION: synthetic peptide

<400> SEQUENCE: 5

Gly Arg Val Asp Pro Ser Asn Lys Ser Met Pro Lys Asp Ile Ala
1               5                   10                  15

<210> SEQ ID NO 6
<211> LENGTH: 10
<212> TYPE: PRT
<213> ORGANISM: Mus musculus

<400> SEQUENCE: 6

Ser Gln Ala Val Gln Glu His Ala Ser Thr
1               5                   10
```

```
<210> SEQ ID NO 7
<211> LENGTH: 13
<212> TYPE: PRT
<213> ORGANISM: Mus musculus

<400> SEQUENCE: 7

Ser Gln Ala Val Gln Glu His Ala Ser Thr Asn Met Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: synthetic peptide

<400> SEQUENCE: 8

Glu Val Ala Gln His Ser Gln Ala Ser Thr Met Asn Gly
1               5                   10

<210> SEQ ID NO 9
<211> LENGTH: 14
<212> TYPE: PRT
<213> ORGANISM: Artificial Sequence
<220> FEATURE:
<223> OTHER INFORMATION: synthetic peptide

<400> SEQUENCE: 9

Gly Gln Ala Ser Ser Ala Gln Met Asn Ser Thr Gly Val His
1               5                   10

<210> SEQ ID NO 10
<211> LENGTH: 18
<212> TYPE: PRT
<213> ORGANISM: Mus musculus

<400> SEQUENCE: 10

Ser Gly Ile Val Ile Tyr Gln Tyr Met Asp Asp Arg Tyr Val Gly Ser
1               5                   10                  15

Asp Leu

<210> SEQ ID NO 11
<211> LENGTH: 11
<212> TYPE: PRT
<213> ORGANISM: Artificial Sequence
<220> FEATURE:
<223> OTHER INFORMATION: synthetic peptide

<400> SEQUENCE: 11

Gly Met Arg Glu Leu Gln Arg Ser Ala Asn Lys
1               5                   10

<210> SEQ ID NO 12
<211> LENGTH: 9
<212> TYPE: PRT
<213> ORGANISM: Mus musculus

<400> SEQUENCE: 12

Val Ile Ile Ile Ala Gln Tyr Met Asp
1               5

<210> SEQ ID NO 13
<211> LENGTH: 15
<212> TYPE: PRT
<213> ORGANISM: Artificial Sequence
<220> FEATURE:
```

```
<223> OTHER INFORMATION: synthetic peptide

<400> SEQUENCE: 13

Met Val Arg Ile Lys Pro Gly Ser Ala Asn Lys Pro Ser Asp Asp
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: synthetic peptide

<400> SEQUENCE: 14

Ser Gln Ala Val Gln Glu His Ala Ser Thr Asn Met Gly
1               5                   10

<210> SEQ ID NO 15
<211> LENGTH: 18
<212> TYPE: PRT
<213> ORGANISM: Artificial Sequence
<220> FEATURE:
<223> OTHER INFORMATION: synthetic peptide

<400> SEQUENCE: 15

Ser Gly Ile Val Ile Tyr Gln Tyr Met Asp Asp Arg Tyr Val Gly Ser
1               5                   10                  15

Asp Leu

<210> SEQ ID NO 16
<211> LENGTH: 9
<212> TYPE: PRT
<213> ORGANISM: Artificial Sequence
<220> FEATURE:
<223> OTHER INFORMATION: synthetic peptide

<400> SEQUENCE: 16

Met Val Arg Ile Lys Pro Gly Ser Ala
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

Val Ile Ile Ile Ala Gln Tyr Met Asp
1               5
```